(12) United States Patent
Smith et al.

(10) Patent No.: US 10,973,931 B2
(45) Date of Patent: Apr. 13, 2021

(54) ADENO-ASSOCIATED VIRAL VECTORS FOR THE GENE THERAPY OF METABOLIC DISEASES

(71) Applicants: UNIVERSITAT AUTONOMA DE BARCELONA, Barcelona (ES); Ulf Per Gustav Smith, Fjaras (SE)

(72) Inventors: Ulf Per Gustav Smith, Fjaras (SE); Fatima Maria Bosch Tubert, Barcelona (ES); Ivet Elias Puigdomenech, Barcelona (ES)

(73) Assignees: Universitat Autònoma de Barcelona, Bellaterra-Barcelona (ES); Ulf Per Gustav Smith, Fjärås (SE)

( * ) Notice: Subject to any disclaimer, the term of this patent is extended or adjusted under 35 U.S.C. 154(b) by 344 days.

(21) Appl. No.: 15/511,599

(22) PCT Filed: Sep. 16, 2014

(86) PCT No.: PCT/EP2014/069743
§ 371 (c)(1),
(2) Date: Mar. 15, 2017

(87) PCT Pub. No.: WO2016/041588
PCT Pub. Date: Mar. 24, 2016

(65) Prior Publication Data
US 2017/0290926 A1    Oct. 12, 2017

(51) Int. Cl.
| | | |
|---|---|---|
| *A61K 48/00* | (2006.01) | |
| *C07K 14/51* | (2006.01) | |
| *C12N 15/86* | (2006.01) | |
| *A61K 38/18* | (2006.01) | |

(52) U.S. Cl.
CPC ...... *A61K 48/0058* (2013.01); *A61K 38/1875* (2013.01); *C07K 14/51* (2013.01); *C12N 15/86* (2013.01); *C12N 2750/14143* (2013.01); *C12N 2750/14151* (2013.01); *C12N 2750/14171* (2013.01); *C12N 2799/025* (2013.01); *C12N 2830/008* (2013.01); *C12N 2830/50* (2013.01)

(58) Field of Classification Search
CPC ............ A61K 48/0058; A61K 38/1875; C12N 15/86; C12N 2799/025; C12N 2750/14171; C12N 2750/14151; C12N 2830/50; C12N 2750/14143; C12N 2830/008
USPC .................. 514/44 R; 424/199.1; 435/320.1; 530/350
See application file for complete search history.

(56) References Cited

U.S. PATENT DOCUMENTS

| | | |
|---|---|---|
| 5,139,941 A | 8/1992 | Muzyczka et al. |
| 5,436,146 A | 7/1995 | Shenk et al. |
| 6,057,152 A | 5/2000 | Samulski et al. |
| 6,136,597 A | 10/2000 | Hope et al. |
| 6,156,303 A | 12/2000 | Russell et al. |
| 6,204,059 B1 | 3/2001 | Samulski et al. |
| 6,268,213 B1 | 7/2001 | Samulski et al. |
| 6,432,705 B1 | 8/2002 | Yee et al. |
| 6,491,907 B1 | 12/2002 | Rabinowitz et al. |
| 6,531,456 B1 | 3/2003 | Kurtzman et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,056,502 B2 | 6/2006 | Hildinger et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,790,449 B2 | 9/2010 | Gao et al. |
| 9,365,829 B2 | 6/2016 | Simpson et al. |
| 2002/0065239 A1 | 5/2002 | Caplan et al. |
| 2003/0219409 A1 | 11/2003 | Coffin et al. |
| 2004/0055023 A1 | 7/2004 | Gao et al. |
| 2005/0187154 A1* | 8/2005 | Kahn ................. A61K 38/1709 514/4.8 |
| 2008/0075740 A1 | 3/2008 | Gao et al. |
| 2010/0216709 A1 | 8/2010 | Scheule et al. |
| 2010/0240029 A1 | 9/2010 | Guarente et al. |
| 2011/0166210 A1 | 7/2011 | Felber et al. |
| 2012/0040401 A1 | 2/2012 | Ellis et al. |
| 2014/0194352 A1 | 7/2014 | Ling et al. |

FOREIGN PATENT DOCUMENTS

| | | |
|---|---|---|
| EP | 2394667 A1 | 12/2011 |
| EP | 2453019 A1 | 5/2012 |

(Continued)

OTHER PUBLICATIONS

NCBI Genbank Accession No. X56848 "M.musculus mRNA for bone morphogenetic protein 4 (BMP-4)", last modified on Sep. 24, 2008.*

(Continued)

*Primary Examiner* — Anne Marie S Wehbe
(74) *Attorney, Agent, or Firm* — N.V. Nederlandsch Octrooibureau; Tamara C. Stegmann; Catherine A. Shultz

(57) ABSTRACT

The present invention discloses adeno-associated viral vectors useful in gene therapy methods for the treatment of obesity, insulin resistance, type 2 diabetes, liver cirrhosis and non-alcoholic fatty liver disease (NAFLD)/non-alcoholic steatohepatitis (NASH). The invention also relates to polynucleotides, plasmids, vectors and methods for the production of such adeno-associated viral vectors. The invention also relates to pharmaceutical compositions comprising said vectors.

14 Claims, 10 Drawing Sheets
Specification includes a Sequence Listing.

(56) References Cited

FOREIGN PATENT DOCUMENTS

| | | |
|---|---|---|
| EP | 2492347 A1 | 8/2012 |
| EP | 2692868 A1 | 2/2014 |
| EP | 3101125 A1 | 12/2016 |
| WO | 199749827 A2 | 12/1997 |
| WO | 98/09524 A1 | 3/1998 |
| WO | 199811244 A2 | 3/1998 |
| WO | 199832869 A1 | 7/1998 |
| WO | 199961601 A2 | 12/1999 |
| WO | 200028004 A1 | 5/2000 |
| WO | 200028061 A2 | 5/2000 |
| WO | 2001083692 A2 | 11/2001 |
| WO | 2001091803 A2 | 12/2001 |
| WO | 2001094605 A2 | 12/2001 |
| WO | 200224234 A2 | 3/2002 |
| WO | 200249423 A1 | 6/2002 |
| WO | 03/052051 A2 | 6/2003 |
| WO | 2003052052 A2 | 6/2003 |
| WO | 2006001982 A2 | 1/2006 |
| WO | 2006110689 A2 | 10/2006 |
| WO | 2007000668 A2 | 1/2007 |
| WO | 2007058902 A1 | 5/2007 |
| WO | 200170276 A2 | 9/2007 |
| WO | 2007127264 A2 | 11/2007 |
| WO | 2008027084 A2 | 3/2008 |
| WO | WO 2008/061011 * | 5/2008 |
| WO | 2008071959 A1 | 6/2008 |
| WO | 2008103755 A1 | 8/2008 |
| WO | 2009120978 A2 | 10/2009 |
| WO | 2009151172 A1 | 12/2009 |
| WO | 2010010887 A1 | 1/2010 |
| WO | 2011004051 A1 | 1/2011 |
| WO | 2011127337 A2 | 10/2011 |
| WO | 2011154520 A1 | 12/2011 |
| WO | WO 2011/154520 * | 12/2011 |
| WO | WO2011/154520 A1 | 12/2011 |
| WO | 2012007458 A1 | 1/2012 |
| WO | 2013006486 A2 | 1/2013 |
| WO | 2013033452 A2 | 3/2013 |
| WO | 2013063379 A1 | 5/2013 |
| WO | 2014012025 A2 | 1/2014 |
| WO | 2014020149 A1 | 2/2014 |
| WO | 2014085365 A2 | 6/2014 |
| WO | WO2015173308 A1 | 11/2015 |
| WO | WO2016193431 A1 | 12/2016 |
| WO | WO2018/060097 A1 | 4/2018 |

OTHER PUBLICATIONS

Hoffman et al. (2014) Diabetologia, vol. 57, Suppl. 1, 51, abstract S566.*
Gray et al. (2012) Design and Construction of Functional AAV Vectors. In: Snyder R., Moullier P. (eds) Adeno-Associated Virus. Methods in Molecular Biology (Methods and Protocols), vol. 807. Humana Press, pp. 25-46.*
Do et al. (2012) Am. J. Physiol. Gastrointest. Liver Physiol., vol. 303:G1220-G1227.*
Lam et al. (2010) Ther. Adv. Gastroenterol., vol. 3(2), 121-137.*
Do, N., et al., "BMP4 is a Novel Paracrine Inhibitor of Liver Regeneration," Am J Physiol. Gastrointest. Liver Physiol., vol. 303, pp. G1220-G1227 (Sep. 27, 2012).
Gustafson, B., et al., "Restricted Adipogenesis in Hypertrophic Obesity the Role of WISP2, WNT, and BMP4," Diabetes, vol. 62, pp. 2997-3004 (Aug. 22, 2013).
Hoffmann, J.M., et al., "Increased BMP4 Improves Insulin Sensitivity and Increases Beige/Brown Adipogenesis in Adult Mice," Diabetologia, vol. 57, Suppl. 1, pp. S1-S566 ( Aug. 29, 2014).
Luk, K., et al., "Adeno-Associated Virus-Mediated Bone Morphogenetic Protein-4 Gene Therapy for In Vivo Bone Formation," Biochemical and Biophysical Research Communications, vol. 308, pp. 636-645 (Aug. 29, 2003).
Vila, L, et al., "AAV8-Mediated Sirt1 Overexpression in the Liver Prevents High-Carbohydrate Diet Induced NAFLD," Diabetologia, vol. 56, Suppl. 1, pp. S1-S566 (Sep. 1, 2013).

Yasunaga, M., et al., "Establishment and Characterization of a Transgenic Mouse Model for In Vivo Imaging of Bmp4 Expression in the Pancreas," PLoS One, vol. 6, Issue 9, e34956, pp. 1-8 (Sep. 15, 2011).
International Search Report of PCT/EP2014/069743 dated May 27, 2015.
Written Opinion of PCT/EP2014/069743 dated May 27, 2015.
Anguela, Xavier M., et al. "Nonviral-mediated hepatic expression of IGF-I increases Treg levels and suppresses autoimmune diabetes in mice." Diabetes 62.2 (2013): 551-560.
Ahi et al, Adenoviral Vector Immunity: Its implications and circumvention strategies. Curr. Gene Ther. vol. 11(4), pp. 307-320, Aug. 2011.
Al-Dossari Mohammad et al, Evaluation of viral and mammalian promoters for driving transgene expression in mouse liver. Biochemical and Biophysical Research Communications vol. 339(2), pp. 673-678, Jan. 13, 2006.
Allera-Moreau et al., Long term expression of bicistronic vector driven by the FGF-1 IRES in mouse muscle. BMC Biotechnology vol. 7, Article 74, Oct. 28, 2007.
Ayuso E, et al, Production, purification and characterization of adeno-associated vectors, Curr. Gene Ther., vol. 10, pp. 423-436, Dec. 1, 2010.
Azzoni AR, The impact of polyadenylation signals on plasmid nuclease-resistance and transgene expression. J Gene Med, vol. 9(5), pp. 392-402, 2007.
Bish L, et al., Adeno-Associated Virus (AAV) Serotype 9 Provides Global Cardiac Gene Transfer Superior to AAV1, AAV6, AAV7, and AAV8 in the Mouse and Rat. Hum. Gene Ther. vol. 19(12), pp. 1359-1368, 2008.
Boulos et al, Assessment of CMV, RSV and SYN1 promoters and the woodchuck post-transcriptional regulatory clement in adenovirus vectors for transgene expression in cortical neuronal cultures. Brain Research vol. 1102, pp. 27-38, 2006.
Brantly et al., Sustained transgene expression despite T lymphocyte responses in a clinical trial of rAAV1-AAT gene therapy. Proc Natl Acad Sci USA vol. 106(38), pp. 16363-368, 2009.
Callejas et al., Treatment of Diabetes and Long-Term Survival After Insulin and Glucokinase Gene Therapy, Diabetes vol. 62(5), pp. 1718-1729, May 1, 2013.
Manno et al., Successful transduction of liver in hemophilia by AAV-Factor IX and limitations imposed by the host Immune response. Nat Med vol. 12(3), pp. 342-347, 2006.
Card et al, MicroRNA silencing improves the tumor specificity of adenoviral transgene expression. Cancer Gene Therapy, vol. 19, pp. 451-459, 2012.
Casteilla Louis et al, Virus-based gene transfer approaches and adipose tissue biology, Current Gene Therapy, vol. 8(2), pp. 79-87, Apr. 2008.
Chen et al, The role of microRNA-1 and microRNA-133 in skeletal muscle proliferation and differentiation. Nature Genetics, vol. 38, pp. 228-233, 2006.
Collaco et al, Monitoring immediate-early gene expression through firefly luciferase imaging of HRS/J hairless mice. BMC Physiol vol. 3(8), epub, Aug. 19, 2003.
Connely and Mech Delivery of Adenoviral DNA to Mouse Liver. From: Methods in Molecular Biology, vol. 246: Gene Delivery to Mammalian Cells: vol. 2: Viral Gene Transfer Technique Edited by: W. C. Heiser © Humana Press Inc., Totowa, NJ, 2004.
Del Mar Gonzalez-Barroso M, et al., Transcriptional Activation of the Human ucp1 Gene in a Rodent Cell Line Synergism of Retinoids, Isoproterenol, and Thiazolidinedione Is Mediated by a Multipartite Response Element. J. Biol. Chem. vol. 275(41), pp. 31722-31732, 2000.
Deng XQ et al, The expression of SIRT1 in nonalcoholic fatty liver disease induced by high-fat diet rats. Liver Int vol. 27, pp. 708-715, 2007.
Doege H. et al , Silencing of hepatic fatty acid transporter protein 5 in vivo reverses diet-induced non-alcoholic fatty liver disease andimproves hyperglycemia, J Biol Chem, 2008, vol. 283(32), pp. 22186-22192, Jun. 3, 2008.
Dong et al., Hepatic insulin production for type 1 diabetes, Trends Endocrinol Metab vol. 12, pp. 441-446, 2001.

(56) References Cited

OTHER PUBLICATIONS

Dressman D., AAV-Mediated Gene Transfer to Models of Muscular Dystrophy: Insights into Assembly of Multi-Subunit Membrane Proteins. University of Pittsburgh, Graduate Faculty of the School of Medicine, Dept. of Biochemistry and Molecular Genetics in partial fulfillment of the requirements for the degree of Doctor of Philosophy. 183 pages, 1997.
Erion D. et al., SirT1 Knockdown in Liver Decreases Basal Hepatic Glucose Production and Increases Hepatic Insulin Responsiveness in Diabetic Rats, PNAS, vol. 106(27), pp. 11288-11293, Jul. 7, 2009.
Fagoe et al, A compact dual promoter adeno-assoicated viral vector for efficient delivery of two genes to dorsal root ganglion neurons. Gene Therapy vol. 21, pp. 242-252, 2014.
Ferrari F et al New developments in the generation of Ad-free, high-titer rAAV gene therapy vectors, vol. 3, pp. 1295-1297, Nov. 1, 1997.
F-L Zhang et al, Celastrol enhances AAV1-mediated gene expression in mice adipose tissues. Gene Therapy vol. 18 (2), pp. 128-134, Feb. 1, 2011.
Florie Borel et al, Recombinant AAV as a Platform for Translating the Therapeutic Potential of RNA Interference. Molecular Therapy vol. 22(4), pp. 692-701, Dec. 19, 2013.
Franckhauser S, et al., Increased Fatty Acid Re-esterification by PEPCK Overexpression in Adipose Tissue Leads to ObesityWithout Insulin Resistance. Diabetes vol. 51, pp. 624-630, 2002.
Gao et al, Novel adeno-associated viruses from rhesus monkeys as vectors for human gene therapy. PNAS vol. 99, pp. 11854-11859, 2002.
Goodwin E.C. and Rottman, F.M., The 3'flanking sequence of the bovine growth hormone gene contains novel elements required for efficient and accurate polyadenylation, J Biol Chem, 1992, 267:16330-16334. Aug. 15, 1992.
Graves RA et al, Identification of a potent adipocyte-specific enhancer: involvement of an NF-1-like factor. Genes & Development vol. 5(3), pp. 428-437. Mar. 1, 1991.
Grunberg et al., The Novel Secreted Adipokine WNT1-inducible Signaling Pathway Protein 2 (WISP2) Is a Mesenchymal Cell Activator of Canonical WNT, Biol Chem, 2014, vol. 289, pp. 6899-6907, Jan. 22, 2014.
Grundy et al, Definition of Metabolic Syndrome Report of the National Heart, Lung, and Blood Institute/American Heart Association Conference on Scientific Issues Related to Definition. Circulation vol. 109, pp. 433-438, 2004.
Grundy et al, Obesity, Metabolic Syndrome, and Coronary Atherosclerosis. Circulation vol. 105, pp. 2696-2698, 2002.
Hafenrichter et al, Quantitative evaluation of liver-specific promoters from retroviral vectors after in vivo transduction of hepatocytes. Blood vol. 84, pp. 3394-3404, 1994.
Hagopian K, et al., Influence of Age and Caloric Restriction on Liver Glycolytic Enzyme Activities and Metabolite Concentrations in Mice. Experimental Gerontology vol. 38, pp. 253-266, Mar. 2003.
Hiroaki Mizukami, Adipose tissue as a novel target for in vivo gene transfer by adeno-associated viral vectors. Human Gene Therapy vol. 17, pp. 921-928. Jan. 2006.
Jaffe et al, Adenovirus-mediated in vivo gene transfer and expression in normal rat liver. Nature Genetics vol. 1(5), pp. 372-378, 1992.
Jimenez et al, In vivo genetic engineering of murine pancreatic beta cells mediated by single-stranded adeno-associated viral vectors of serotypes 6, 8 and 9. Diabetologia ; Clinical and Experimental, Diabetes and Metabolism, Springer, Berlin, DE, vol. 54(5), pp. 1075-1086, Feb. 11, 2011.
Kapturczak et al., Transduction of Human and Mouse Pancreatic Islet Cells Using a Bicistronic Recombinant Adeno-associated Viral Vector. Molecular Therapy vol. 5(2), pp. 154-160, Feb. 2002.
Kelly and Russell MicroRNAs and the Regulation of Vector Tropism. Molecular Therapy vol. 17(3), pp. 409-416, 2009.
Kim et al, Genebank NP_001104746.1, insulin-like growth factor 1 isoform 5 preproprotein [Mus musculus], Dec. 2007.
Kitajima et al, Persistent liver expression of murine apoA-I using vectors based on adeno-associated viral vectors serotypes 5 and 1. Atherosclerosis vol. 186, pp. 65-73, 2006.
Kojima et al., NeuroD-betacellulin gene therapy induces islet neogenesis in the liver and reverses diabetes in mice. Nat Med vol. 9, pp. 596-603. Epub 2003 Apr. 2021, 2003.
Kotronen et al, Fatty Liver a Novel Component of the Metabolic Syndrome. Arterioscler Thromb Vasc Biol vol. 28, pp. 27-38, 2008.
Lagos-Quintana et al, Identification of Tissue-Specific MicroRNAs from Mouse. Current Biology vol. 12, pp. 735-739, Apr. 2002.
Lee et al, Optimizing regulatable gene expression using adenoviral vectors. Experimental Physiology vol. 90, pp. 33-37, 2004.
Li et al, A small regulatory element from chromosome 19 enhances liver-specific gene expression. Gene Therapy 16, pp. 43-51 2009.
Li Yu et al, Hepatic overexpression of SIRT1 in mice attenuates endoplasmic reticulum stress and insulin resistance in the liver. Faseb Journal, Official Publication of the Federation of American Societies for Experimental Biology, vol. 25 (5), pp. 1664-1679, May 2011.
Liu et al, Promoter effects of adeno-associated viral vector for transgene expression in the cochlea in vivo. Experimental and Molecular Medicine vol. 39, pp. 170-175, 2007.
Mann et al, Gene therapy for type 1 diabetes by engineering skeletal muscle to express insulin and glucokinase (GK): Pre-clinical studies in diabetic. Diabetes (online), pp. A125-A126, Jun. 1, 2008.
Mas et al., Reversal of type 1 diabetes by engineering a glucose sensor in skeletal muscle. Diabetes vol. 55(6), pp. 1546-1553, Jun. 2006.
Zincarelli et al, Analysis of AAV serotypes 1-9 mediated gene expression and tropism in mice after systemic injection. Mol Ther vol. 16(6), pp. 1073-1080, 2008.
Masferrer, Estudi En Animals Transgenics Del Paper De La Gk En El Control De L'Homeostasi De La Glucosa. Implicacions En La Terapia Genica De La Diabetis Mellitus. May 1998.
Mingozzi et al, Induction of immune tolerance to coagulation factor IX antigen by in vivo hepatic gene transfer. J. Ciin Invest, vol. 111, pp. 1347-1356, 2003.
Zhang H, et al., Adenovirus-adeno-associated virus hybrid for large-scale recombinant adeno-associated virus production., Hum. Gene Ther., vol. 20, pp. 922-929, Aug. 6, 2009.
Monica George et al, [beta] cell expression of IGF-I leads to recovery from type 1 diabetes. Journal of Clinical Investigation vol. 109 (9), pp. 1153-1163, May 2002.
Nakai H, et al., Unrestricted Hepatocyte Transduction with Adeno-Associated VirusSerotype 8 Vectors in Mice. J. Virol. vol. 79, pp. 214-224, 2005.
Nathwani et al, Safe and efficient transduction of the liver after peripheral vein infusion of self-complementary AAV rector results in stable therapeutic expression of human FIX in nonhuman primates. Blood vol. 109, pp. 1414-1421, 2007.
O'Brien et al., Gene Therapy for Type 1 Diabetes Moves a Step Closer to Reality. Diabetes vol. 62(5): 1396-1397, May 2013.
Okada T et al, Scalable purification of adeno-associated virus serotype 1 (AAV1) and AAV8 vectors, using dual ion-exchange adsorptive membranes., Hum. Gene Ther., vol. 20, pp. 1013-1021, Aug. 5, 2009.
Orellana-Gavalda et al., Molecular therapy for obesity and diabetes based on a long-term increase in hepatic fatty-acid oxidation, Hepatology, 2011, vol. 53(3), pp. 821-832, Dec. 10, 2010.
Otaegui et al, Prevention of obesity and insulin resistance by glucokinase expression in skeletal muscle of transgenic mice. The FASEB Journal express article. Online 10.1096/fj.03-0081fje, Sep. 18, 2003.
Parsons et al, Ectopic expression of glucagon-like peptide 1 for gene therapy of type II diabetes. Gene Therapy vol. 14(1), pp. 38-48, Jan. 1, 2007.
Pfluger et al, Sirt1 protects against high-fat diet-induced metabolic damage. PNAS vol. 105, pp. 9793-9798, 2008.
Pinkert et al, An albumin enhancer located 10 kb upstream functions along with its promoter to direct efficient, liver-specific expression in transgenic mice. Genes Dev. vol. 1(3), pp. 268-277, 1987.

(56) References Cited

OTHER PUBLICATIONS

Purushotham et al, Hepatocyte-Specific Deletion of SIRT1 Alters Fatty Acid Metabolism and Results in Hepatic Steatosis and Inflammation. Cell Metabolism, vol. 9, pp. 327-338, Apr. 8, 2009.
Qiao C et al, Liver-specific microRNA-122 target sequences incorporated in AAV vectors efficiently inhibits transgene expression in the liver, Gene Therapy vol. 18(4), pp. 403-410, Apr. 1, 2011.
Rui et al, Counteraction of Type 1 Diabetic Alterations by Engineering Skeletal Muscle to Produce Insulin Insights from Transgenic Mice, Diabetes vol. 51 pp. 704-711, Mar. 2002.
Sharp et al, The codon adaptation index—A measure of directional synonymous codon usage bias, and its potential applications. Nucleic Acids Research vol. 15(3), pp. 1281-1295, Feb. 11, 1987.
Smith et al., The Structure of T6 Human Insulin at 1.0 A Resolution. Ada Crystallographica Section D, Biological Crystallography, Research Papers, D59, pp. 474-482, 2003.
Snyder R et al. Persistent and therapeutic concentrations of human factor IX in mice after hepatic transfer of recombinant AAV vectors, Nature Genetics, pp. 270-276, Jul. 16, 1997.
Tae Keun Oh et al, Gene therapy for diabetes mellitus in rats by intramuscular injection of lentivirus containing insulin gene. Diabetes Research and Clinical Practice vol. 71(3), pp. 233-240, Mar. 1, 2006.
Tian et al, Independent and high-level dual-gene expression in adult stem-progenitor cells from a single lentiviral iector. Gene Therapy vol. 16, pp. 874-884, 2009.
Urabe et al, A novel dicistronic AAV vector using a short IRES segment derived from hepatitis C virus genome. Gene vol. 200, pp. 157-162, 1997.
Van Linthout S et al, Persistent hepatic expression of human apo A-I after transfer with a helper-virus independent adenoviral vector Gene Therapy vol. 9(22), pp. 1520-1528, Nov. 2002.
Vila GBP et al, 237: AAV8-mediated Sirt1 overexpression in the liver prevents high-carbohydrate diet induced NAFLD. Diabetologia, 49th Annual Meeting of the European Association for the Study of Diabetes, Springer, Berlin, DE; Barcelona, Spain, vol. 56, Suppl. 1, p. S105, Sep. 27, 2013.
Vila L. et al, Suppressor of Cytokine Signaling-3 (SOCS-3) and aDeficit of Serine/Threonine (Ser/Thr) PhosphoproteinsInvolved in Leptin Transduction Mediate the Effect ofFructose on Rat Liver Lipid Metabolism. Hepatology vol. 48, pp. 1506-1516, 2008.
Virag T, et al, Producing recombinant adeno-associated virus in foster cells: overcoming production limitations using a baculovirus-insect cell expression strategy, Hum. Gene Ther., vol. 20, pp. 807-817, Jul. 29, 2009.
Wang et al, Liver Steatosis and Increased ChREBP Expression in Mice Carrying a Liver Specific SIRT1 Null Mutation under a Normal Feeding Condition. Int J Biol Sci, vol. 6, pp. 682-690, 2010.
Wang et al, Widespread and Stable Pancreatic Gene Transfer by Adeno-Associated Virus Vectors via Different Routes, Diabetes vol. 55, pp. 875-884, Apr. 2006.
Wang et al., Bone Morphogenetic Protein (BMP) signaling in development and human diseases, Genes Dis., vol. 1, No. 1, pp. 87-105. Jul. 15, 2014.
World Health Organization, Definition and diagnosis of diabetes mellitus and intermediate hyperglycemia: report of a WHO/IDF consultation, 2006.
Wu et al, Mutational analysis of the adeno-associated virus type 2 (AAV2) capsid gene and construction of AAV2 vectors with altered tropism. J. Vir. vol. 74, pp. 8635-8647, 2000.
Xie et al, MicroRNA-regulated, Systemically Delivered rAAV9: A Step Closer to CNS-restricted Transgene Expression. Molecular Therapy, Nature Publishing Group, GB, vol. 19(3), pp. 526-535, Mar. 2011.
Yan et al, Inverted Terminal Repeat Sequences are Important for Intermolecular Recombination and Circularization of Adeno-Associated Virus Genomes. Journal of Virology, vol. 79, pp. 364-379, 2005.
Yi Liu et al, A one-step cloning method for the construction of somatic cell gene targeting vectors: application to production of human knockout cell lines. BMC Biotechnology vol. 12(1), p. 71, Oct. 9, 2012.
Yoon et al, Neuroprotective effects of molecular chaperones and anti-apoptotic genes BAG1, PINK1 and SIRT1 overexpression in rat models of Parkinson's disease, 38th Annual Meeting of the Society-for-Neuroscience; Washington DC, USA, vol. 38(18), Nov. 15, 2008.
Zarrin et al, Comparison of CMV, RSV, SV40 viral and Vlambda1 cellular promoters in B and T lymphoid and non-lymphoid cell lines. Biochimica and Physica Acta vol. 1446, pp. 135-139, 1999.
Zhang et al, Adipose Tissue Transduction Using AAv8-Based Vectors: Inadvertent Gene Transfer into Liver. Molecular Therapy, vol. 11 (S1), article 862, 2005.

* cited by examiner

A)

B)

C)

A)

B)

A)

B)

SEQUENCE LISTING

<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: Kozak sequence

<400> SEQUENCE: 1
gccaccatgg                                                          10

```
<210> SEQ ID NO 2
<211> LENGTH: 133
<212> TYPE: DNA
<213> ORGANISM: adeno-associated virus 2

<400> SEQUENCE: 2
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt cct                                                         133

<210> SEQ ID NO 3
<211> LENGTH: 141
<212> TYPE: DNA
<213> ORGANISM: adeno-associated virus 2

<400> SEQUENCE: 3
aggaacccct agtgatggag ttggccactc cctctctgcg cgctcgctcg ctcactgagg      60
ccgggcgacc aaaggtcgcc cgacgcccgg gctttgcccg gcggcctca gtgagcgagc      120 gagcgcgcca gctggcgtaa t                                                141

<210> SEQ ID NO 4
<211> LENGTH: 1094
<212> TYPE: DNA
<213> ORGANISM: Artificial Sequence
<220> FEATURE:
<223> OTHER INFORMATION: liver-specific transcriptional-regulatory
      region HCR-hAAT

<400> SEQUENCE: 4
gatctgatat catcgatgaa ttcgagctcg gtacccggcc gcagatttag gtgacactat      60
agaatatgca tcactagtaa gcttgcgaat tccagtctac agagaggtct ctgacctctg     120
ccccagctcc aaggtcagca ggcagggagg ctgtgtgtt tgctgtttgc tgcttgcaat      180
gtttgcccat tttagggaca tgagtaggct gaagtttgtt cagtgtggac ttcagaggca     240
gcacacaaac agcaagcttg cgaattccag tctacagaga ggtctctgac ctctgcccca     300
gctccaaggt cagcaggcag ggagggctgt gtgtttgctg tttgctgctt gcaatgtttg     360
cccattttag ggacatgagt aggctgaagt tgttcagtg tggacttcag aggcagcaca     420
caaacagcaa gcttgcgaat tccagtctac agagaggtct ctgacctctg ccccagctcc     480
aaggtcagca ggcagggagg ctgtgtgtt tgctgtttgc tgcttgcaat gtttgcccat      540
tttagggaca tgagtaggct gaagtttgtt cagtgtggac ttcagaggca gcacacaaac     600
agcaagcttt gctctagact ggaattcgtc gacgagctcc ctatagtgag tcgtattaga     660
ggccgactga cccggtaccc gggatcttg ctaccagtgg aacagccact aaggattctg      720
cagtgagagc agagggccag ctaagtggta ctctcccaga gactgtctga ctcacgccac     780
cccctccacc ttggacacag gacgctgtgg tttctgagcc aggtacaatg actcctttcg     840
gtaagtgcag tggaagctgt acactgccca ggcaaagcgt ccgggcagcg taggcgggcg     900
actcagatcc cagccagtgg acttagcccc tgtttgctcc tccgataact ggggtgacct     960
tggttaatat tcaccagcag cctcccccgt tgccctctg gatccactgc ttaaatacgg     1020
acgaggacag ggccctgtct cctcagcttc aggcaccacc actgacctgg gacagtgaat    1080 gtcccccctga tctg                                                     1094
```

<210> SEQ ID NO 5
<211> LENGTH: 85
<212> TYPE: DNA
<213> ORGANISM: Artificial Sequence
<220> FEATURE:
<223> OTHER INFORMATION: intron

<400> SEQUENCE: 5

```
aggcactggg caggtaagta tcaaggttac aagacaggtt taaggagacc aatagaaact    60
gggcttgtcg agacagagaa gactc                                          85
```

<210> SEQ ID NO 6
<211> LENGTH: 1227
<212> TYPE: DNA
<213> ORGANISM: Mus musculus

<400> SEQUENCE: 6

```
atgattcctg gtaaccgaat gctgatggtc gttttattat gccaagtcct gctaggaggc     60
gcgagccatg ctagtttgat acctgagacc gggaagaaaa aagtcgccga gattcagggc    120
cacgcgggag gacgccgctc agggcagagc catgagctcc tgcgggactt cgaggcgaca    180
cttctacaga tgtttgggct gcgccgccgt ccgcagccta gcaagagcgc cgtcattccg    240
gattacatga gggatcttta ccggctccag tctggggagg aggaggagga agagcagagc    300
cagggaaccg ggcttgagta cccggagcgt cccgccagcc gagccaacac tgtgaggagt    360
ttccatcacg aagaacatct ggagaacatc ccagggacca gtgagagctc tgcttttcgt    420
ttcctcttca acctcagcag catcccgaga aatgaggtga tctcctcggc agagctccgg    480
ctctttcggg agcaggtgga ccagggccct gactgggaac agggcttcca ccgtataaac    540
atttatgagg ttatgaagcc cccagcagaa atggttcctg acacctcat cacacgacta    600 ctggacacca gactagtcca tcacaatgtg acacggtggg aaactttcga tgtgagccct    660
gcagtccttc gctggaccccg ggaaaagcaa cccaattatg ggctggccat tgaggtgact    720
cacctccacc agacacggac ccaccagggc cagcacgtca gaatcagccg atcgttacct    780
caagggagtg gagattgggc ccaactccgg cccctcctgg tcacttttgg ccatgatggc    840
cggggccata ccttgacccg cagaagggcc aaacgtagtc ccaagcatca cccacagcgg    900
tccaggaaga gaataagaa ctgccgtcgc cattcactat acgtggactt cagtgacgtg    960
ggctggaatg attggattgt ggccccaccc ggctaccagg ccttctactg ccacgggac    1020 tgtccctttc cactggctga tcacctcaac tcaaccaacc atgccattgt gcagacccta    1080
gtcaactctg ttaattctag tatccctaag gcctgttgtg tccccactga actgagtgcc    1140
atttccatgt tgtacctgga tgagtatgac aaggtggtgt tgaaaaatta tcaggagatg    1200
gtggtagagg ggtgtggatg ccgctga                                        1227
```

<210> SEQ ID NO 7
<211> LENGTH: 1253
<212> TYPE: DNA
<213> ORGANISM: Artificial Sequence
<220> FEATURE:
<223> OTHER INFORMATION: variant of mouse BMP4

<400> SEQUENCE: 7

```
ccgggctcga ggccaccatg atccctggca acagaatgct gatggtggtg ctgctgtgcc     60
aggtgctgct gggcggagct tctcacgcca gcctgatccc cgagacaggc aagaaaaagg    120
tggccgagat ccagggccac gctggcggca gaagatctgg ccagtctcac gagctgctga    180
```

-continued

| | |
|---|---|
| gagacttcga ggctaccctg ctgcagatgt tcggcctgag aagaaggccc cagcccagca | 240 |
| agtctgccgt gatccctgac tacatgaggg acctgtacag actgcagagc ggcgaggaag | 300 |
| aggaagaaga acagtcccag ggcaccggcc tggaataccc tgaaagacct gccagcagag | 360 |
| ccaacaccgt gcgcagcttc caccacgagg aacacctgga aaacatcccc ggcaccagcg | 420 |
| agagcagcgc cttcagattc ctgttcaacc tgagcagcat ccctgagaac gaagtgatca | 480 |
| gcagcgccga gctgagactg ttcagagaac aggtggacca gggcccccgat gggagcagg | 540 |
| gcttccacag aatcaacatc tatgaagtga tgaagccccc tgccgagatg gtgcccggcc | 600 |
| acctgattac cagactgctg acaccagac tggtgcatca aacgtgacc agatgggaga | 660 |
| cattcgacgt gtccccagcc gtgctgagat ggaccagaga aagcagccc aactacggcc | 720 |
| tggccatcga agtgacccat ctgcaccaga ccagaaccca ccaggacag cacgtgcgga | 780 |
| tcagcagatc tctgcctcag ggctctggcg attgggccca gctgaggcca ctgctcgtga | 840 |
| catttggcca cgacggcaga ggccacaccc tgaccgaaag aagggccaag agaagcccca | 900 |
| agcaccaccc ccagagatcc agaaagaaaa acaagaactg caggcggcac agcctgtacg | 960 |
| tggacttctc tgacgtgggc tggaacgact ggatcgtggc ccctcctggc taccaggcct | 1020 |
| tctactgtca cggcgactgc cccttccctc tggccgacca cctgaacagc accaaccacg | 1080 |
| ccatcgtgca gaccctcgtg aacagcgtga actccagcat ccccaaggcc tgctgcgtgc | 1140 |
| caacagagct gagcgccatc tccatgctgt acctggacga gtacgacaaa gtggtgctga | 1200 |
| agaactacca ggaaatggtg gtggaaggct gtggctgtag atgaacgcgt ccc | 1253 |

<210> SEQ ID NO 8
<211> LENGTH: 1227
<212> TYPE: DNA
<213> ORGANISM: Homo sapiens

<400> SEQUENCE: 8

| | |
|---|---|
| atgattcctg gtaaccgaat gctgatggtc gttttattat gccaagtcct gctaggaggc | 60 |
| gcgagccatg ctagtttgat acctgagacg gggaagaaaa aagtcgccga gattcagggc | 120 |
| cacgcgggag gacgccgctc agggcagagc catgagctcc tgcgggactt cgaggcgaca | 180 |
| cttctgcaga tgtttgggct gcgccgccgc ccgcagccta gcaagagtgc cgtcattccg | 240 |
| gactacatgc gggatctttta ccggcttcag tctggggagg aggaggaaga gcagatccac | 300 |
| agcactggtc ttgagtatcc tgagcgcccg gccagccggg ccaacaccgt gaggagcttc | 360 |
| caccacgaag aacatctgga gaacatccca gggaccagtg aaaactctgc ttttcgtttc | 420 |
| ctctttaacc tcagcagcat ccctgagaac gaggtgatct cctctgcaga gcttcggctc | 480 |
| ttccgggagc aggtggacca gggccctgat tgggaaaggg gcttccaccg tataaacatt | 540 |
| tatgaggtta tgaagccccc agcagaagtg gtgcctgggc acctcatcac acgactactg | 600 |
| gacacgagac tggtccacca caatgtgaca cggtgggaaa cttttgatgt gagccctgcg | 660 |
| gtccttcgct ggaccccggga gaagcagcca aactatgggc tagccattga ggtgactcac | 720 |
| ctccatcaga ctcggaccca ccagggccag catgtcagga ttagccgatc gttacctcaa | 780 |
| gggagtggga attgggccca gctccggccc ctcctggtca cctttggcca tgatggccgg | 840 |
| ggccatgcct tgacccgacg ccggagggcc aagcgtagcc ctaagcatca ctcacagcgg | 900 |
| gccaggaaga gaataagaa ctgccggcgc cactcgctct atgtggactt cagcgatgtg | 960 |
| ggctggaatg actggattgt ggccccacca ggctaccagg ccttctactg ccatgggac | 1020 |
| tgcccctttc cactggctga ccacctcaac tcaaccaacc atgccattgt gcagaccctg | 1080 |

```
gtcaattctg tcaattccag tatccccaaa gcctgttgtg tgcccactga actgagtgcc    1140
atctccatgc tgtacctgga tgagtatgat aaggtggtac tgaaaaatta tcaggagatg    1200
gtagtagagg gatgtgggtg ccgctga                                        1227

<210> SEQ ID NO 9
<211> LENGTH: 167
<212> TYPE: DNA
<213> ORGANISM: Artificial Sequence
<220> FEATURE:
<223> OTHER INFORMATION: SV40poly A

<400> SEQUENCE: 9
cggccgcttc cctttagtga gggttaatgc ttcgagcaga catgataaga tacattgatg      60
agtttggaca aaccacaact agaatgcagt gaaaaaaatg ctttatttgt gaaatttgtg     120
atgctattgc tttatttgta accattataa gctgcaataa acaagtt                  167

<210> SEQ ID NO 10
<211> LENGTH: 3300
<212> TYPE: DNA
<213> ORGANISM: Artificial Sequence
<220> FEATURE:
<223> OTHER INFORMATION: ITR-hAAT-mouse BMP4-SV40polyA-ITR

<400> SEQUENCE: 10
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtagccatgc     180
tctagacatg gctcgacaga tctgatatca tcgatgaatt cgagctcggt acccggccgc     240
agatttaggt gacactatag aatatgcatc actagtaagc ttgcgaattc cagtctacag     300
agaggtctct gacctctgcc ccagctccaa ggtcagcagg cagggagggc tgtgtgtttg     360
ctgtttgctg cttgcaatgt ttgcccattt tagggacatg agtaggctga agtttgttca     420
gtgtggactt cagaggcagc acacaaacag caagcttgcg aattccagtc tacagagagg     480
tctctgacct ctgccccagc tccaaggtca gcaggcaggg agggctgtgt gtttgctgtt     540
tgctgcttgc aatgtttgcc catttaggg acatgagtag gctgaagttt gttcagtgtg      600
gacttcagag gcagcacaca aacagcaagc ttgcgaattc cagtctacag agaggtctct     660
gacctctgcc ccagctccaa ggtcagcagg cagggagggc tgtgtgtttg ctgtttgctg     720
cttgcaatgt ttgcccattt tagggacatg agtaggctga agtttgttca gtgtggactt     780
cagaggcagc acacaaacag caagctttgc tctagactgg aattcgtcga cgagctccct     840
atagtgagtc gtattagagg ccgactgacc cggtacccgg ggatcttgct accagtggaa     900
cagccactaa ggattctgca gtgagagcag agggccagct aagtggtact ctcccagaga     960
ctgtctgact cacgccaccc cctccacctt ggacacagga cgctgtggtt tctgagccag    1020
gtacaatgac tcctttcggt aagtgcagtg gaagctgtac actgcccagg caaagcgtcc    1080
gggcagcgta ggcgggcgac tcagatccca gccagtggac ttagcccctg tttgctcctc    1140
cgataactgg ggtgaccttg gttaatattc accagcagcc tcccccgttg ccctctggga    1200
tccactgctt aaatacggac gaggacaggg ccctgtctcc tcagcttcag gcaccaccac    1260
tgacctggga cagtgaatgt cccccctgatc tgcggccgtg actctcttaa ggtagccttg    1320
cagaagttgg tcgtgaggca ctgggcaggt aagtatcaag gttacaagac aggtttaagg    1380
agaccaatag aaactgggct tgtcgagaca gagaagactc ttgcgtttct gataggcacc    1440
```

```
tattggtctt actgacatcc actttgcctt tctctccaca ggtgtccact cccagttcaa   1500
ttacagctct taaggctaga gtacttaata cgactcacta taggctagcc tcgacctcga   1560
gatgattcct ggtaaccgaa tgctgatggt cgttttatta tgccaagtcc tgctaggagg   1620
cgcgagccat gctagtttga tacctgagac cgggaagaaa aaagtcgccg agattcaggg   1680
ccacgcggga ggacgccgct cagggcagag ccatgagctc ctgcgggact tcgaggcgac   1740
acttctacag atgtttgggc tgcgccgccg tccgcagcct agcaagagcg ccgtcattcc   1800
ggattacatg agggatcttt accggctcca gtctggggag gaggaggagg aagagcagag   1860
ccagggaacc gggcttgagt acccggagcg tcccgccagc cgagccaaca ctgtgaggag   1920
tttccatcac gaagaacatc tggagaacat cccagggacc agtgagagct ctgcttttcg   1980
tttcctcttc aacctcagca gcatcccaga gaatgaggtg atctcctcgg cagagctccg   2040
gctctttcgg gagcaggtgg accagggccc tgactgggaa cagggcttcc accgtataaa   2100
catttatgag gttatgaagc ccccagcaga aatggttcct ggacacctca tcacacgact   2160
actggacacc agactagtcc atcacaatgt gacacgtgg gaaactttcg atgtgagccc   2220
tgcagtcctt cgctggaccc gggaaaagca acccaattat gggctggcca ttgaggtgac   2280
tcacctccac cagacacgga cccaccaggg ccagcacgtc agaatcagcc gatcgttacc   2340
tcaagggagt ggagattggg cccaactccg gcccctcctg gtcacttttg gccatgatgg   2400 ccgggggccat accttgaccc gcagaagggc caaacgtagt cccaagcatc acccacagcg   2460
gtccaggaag aagaataaga actgccgtcg ccattcacta tacgtggact tcagtgacgt   2520
gggctggaat gattggattg tggccccacc cggctaccag gccttctact gccacgggga   2580 ctgtccctt ccactggctg atcacctcaa ctcaaccaac catgccattg tgcagaccct   2640
agtcaactct gttaattcta gtatccctaa ggcctgttgt gtccccactg aactgagtgc   2700
catttccatg ttgtacctgg atgagtatga caaggtggtg ttgaaaaatt atcaggagat   2760
ggtggtagag gggtgtggat gccgctgaac gcgtgatatc ggatcccggc cggcggccgc   2820 ttcccttag tgagggttaa tgcttcgagc agacatgata agatacattg atgagtttgg   2880
acaaaccaca actagaatgc agtgaaaaaa atgctttatt tgtgaaattt gtgatgctat   2940
tgctttattt gtaaccatta taagctgcaa taaacaagtt aacaacaaca attgcattca   3000
ttttatgttt caggttcagg gggagatgtg ggaggttttt taaagcaagt aaaacctcta   3060
caaatgtggt aaaatccgat aagggactag agcatggcta cgtagataag tagcatggcg   3120
ggttaatcat taactacaag gaaccctag tgatggagtt ggccactccc tctctgcgcg   3180
ctcgctcgct cactgaggcc gggcgaccaa aggtcgcccg acgcccgggc tttgcccggg   3240
cggcctcagt gagcgagcga gcgcgccagc tggcgtaata gcgaagaggc ccgcaccgat   3300
```

<210> SEQ ID NO 11
<211> LENGTH: 3306
<212> TYPE: DNA
<213> ORGANISM: Artificial Sequence
<220> FEATURE:
<223> OTHER INFORMATION: ITR-hAAT-mouse BMP4 variant-SV40polyA-ITR

<400> SEQUENCE: 11

```
cagctgcgcg ctcgctcgct cactgaggcc gcccgggcaa agcccgggcg tcgggcgacc     60
tttggtcgcc cggcctcagt gagcgagcga gcgcgcagag agggagtggc caactccatc    120
actaggggtt ccttgtagtt aatgattaac ccgccatgct acttatctac gtagccatgc    180
tctagacatg gctcgacaga tctgatatca tcgatgaatt cgagctcggt acccggccgc    240
```

```
agatttaggt gacactatag aatatgcatc actagtaagc ttgcgaattc cagtctacag    300
agaggtctct gacctctgcc ccagctccaa ggtcagcagg cagggagggc tgtgtgtttg    360
ctgtttgctg cttgcaatgt ttgcccattt tagggacatg agtaggctga agtttgttca    420
gtgtggactt cagaggcagc acacaaacag caagcttgcg aattccagtc tacagagagg    480
tctctgacct ctgccccagc tccaaggtca gcaggcaggg agggctgtgt gtttgctgtt    540
tgctgcttgc aatgtttgcc cattttaggg acatgagtag gctgaagttt gttcagtgtg    600
gacttcagag gcagcacaca aacagcaagc ttgcgaattc cagtctacag agaggtctct    660
gacctctgcc ccagctccaa ggtcagcagg cagggagggc tgtgtgtttg ctgtttgctg    720
cttgcaatgt ttgcccattt tagggacatg agtaggctga agtttgttca gtgtggactt    780
cagaggcagc acacaaacag caagctttgc tctagactgg aattcgtcga cgagctccct    840
atagtgagtc gtattagagg ccgactgacc cggtacccgg ggatcttgct accagtggaa    900
cagccactaa ggattctgca gtgagagcag agggccagct aagtggtact ctcccagaga    960
ctgtctgact cacgccaccc cctccacctt ggacacagga cgctgtggtt tctgagccag   1020
gtacaatgac tcctttcggt aagtgcagtg gaagctgtac actgcccagg caaagcgtcc   1080
gggcagcgta ggcgggcgac tcagatccca gccagtggac ttagcccctg tttgctcctc   1140
cgataactgg ggtgaccttg gttaatattc accagcagcc tcccccgttg ccctctgga   1200 tccactgctt aaatacggac gaggacaggg ccctgtctcc tcagcttcag gcaccaccac   1260
tgacctggga cagtgaatgt cccctgatc tgcggccgtg actctcttaa ggtagccttg   1320
cagaagttgg tcgtgaggca ctgggcaggt aagtatcaag gttacaagac aggtttaagg   1380
agaccaatag aaactgggct tgtcgagaca gagaagactc ttgcgtttct gataggcacc   1440
tattggtctt actgacatcc actttgcctt tctctccaca ggtgtccact cccagttcaa   1500
ttacagctct taaggctaga gtacttaata cgactcacta taggctagcc tcgacctcga   1560
ggccaccatg atccctggca acagaatgct gatggtggtg ctgctgtgcc aggtgctgct   1620
gggcggagct tctcacgcca gcctgatccc cgagacaggc aagaaaaagg tggccgagat   1680
ccagggccac gctggcggca aagatctgg ccagtctcac gagctgctga gagacttcga   1740
ggctaccctg ctgcagatgt tcggcctgag aagaaggccc cagcccagca gtctgccgt   1800 gatccctgac tacatgaggg acctgtacag actgcagagc ggcgaggaag aggaagaaga   1860
acagtcccag ggcaccggcc tggaataccc tgaaagacct gccagcagag ccaacaccgt   1920
gcgcagcttc caccacgagg aacacctgga aacatccccc ggcaccagcg agagcagcgc   1980
cttcagattc ctgttcaacc tgagcagcat ccctgagaac gaagtgatca gcagcgccga   2040
gctgagactg ttcagagaac aggtggacca gggccccgat tgggagcagg cttccacag   2100 aatcaacatc tatgaagtga tgaagccccc tgccgagatg gtgcccggcc acctgattac   2160
cagactgctg gacaccagac tggtgcatca acgtgacc agatgggaga cattcgacgt   2220
gtccccagcc gtgctgagat ggaccagaga gaagcagccc aactacggcc tggccatcga   2280
agtgacccat ctgcaccaga ccagaaccca ccagggacag cacgtgcgga tcagcagatc   2340
tctgcctcag ggctctggcg attgggccca gctgaggcca ctgctcgtga catttggcca   2400
cgacggcaga ggccacaccc tgaccagaag aagggccaag agaagcccca gcaccaccc   2460 ccagagatcc agaaagaaaa acaagaactg caggcggcac agcctgtacg tggacttctc   2520
tgacgtgggc tggaacgact ggatcgtggc ccctcctggc taccaggcct tctactgtca   2580
cggcgactgc ccttccctc tggccgacca cctgaacagc accaaccacg ccatcgtgca   2640
```

| | |
|---|---|
| gaccctcgtg aacagcgtga actccagcat ccccaaggcc tgctgcgtgc aacagagct | 2700 |
| gagcgccatc tccatgctgt acctggacga gtacgacaaa gtggtgctga agaactacca | 2760 |
| ggaaatggtg gtggaaggct gtggctgtag atgaacgcgt gatatcggat cccggccggc | 2820 |
| ggccgcttcc ctttagtgag ggttaatgct tcgagcagac atgataagat acattgatga | 2880 |
| gtttggacaa accacaacta gaatgcagtg aaaaaaatgc tttatttgtg aaatttgtga | 2940 |
| tgctattgct ttatttgtaa ccattataag ctgcaataaa caagttaaca acaacaattg | 3000 |
| cattcatttt atgtttcagg ttcaggggga gatgtgggag gttttttaaa gcaagtaaaa | 3060 |
| cctctacaaa tgtggtaaaa tccgataagg gactagagca tggctacgta gataagtagc | 3120 |
| atggcgggtt aatcattaac tacaaggaac ccctagtgat ggagttggcc actccctctc | 3180 |
| tgcgcgctcg ctcgctcact gaggccgggc gaccaaaggt cgcccgacgc ccgggctttg | 3240 |
| cccgggcggc ctcagtgagc gagcgagcgc gccagctggc gtaatagcga agaggcccgc | 3300 |
| accgat | 3306 |

<210> SEQ ID NO 12
<211> LENGTH: 3300
<212> TYPE: DNA
<213> ORGANISM: Artificial Sequence
<220> FEATURE:
<223> OTHER INFORMATION: ITR-hAAT-human BMP4-SV40polyA-ITR

<400> SEQUENCE: 12

| | |
|---|---|
| cagctgcgcg ctcgctcgct cactgaggcc gcccgggcaa agcccgggcg tcgggcgacc | 60 |
| tttggtcgcc cggcctcagt gagcgagcga gcgcgcagag agggagtggc caactccatc | 120 |
| actagggtt ccttgtagtt aatgattaac ccgccatgct acttatctac gtagccatgc | 180 |
| tctagacatg gctcgacaga tctgatatca tcgatgaatt cgagctcggt acccggccgc | 240 |
| agatttaggt gacactatag aatatgcatc actagtaagc ttgcgaattc cagtctacag | 300 |
| agaggtctct gacctctgcc ccagctccaa ggtcagcagg cagggagggc tgtgtgtttg | 360 |
| ctgtttgctg cttgcaatgt tgcccatttt agggacatg agtaggctga agtttgttca | 420 |
| gtgtggactt cagaggcagc acacaaacag caagcttgcg aattccagtc tacagagagg | 480 |
| tctctgacct ctgccccagc tccaaggtca gcaggcaggg agggctgtgt gtttgctgtt | 540 |
| tgctgcttgc aatgtttgcc cattttaggg acatgagtag gctgaagttt gttcagtgtg | 600 |
| gacttcagag gcagcacaca aacagcaagc ttgcgaattc cagtctacag agaggtctct | 660 |
| gacctctgcc ccagctccaa ggtcagcagg caggagggc tgtgtgtttg ctgtttgctg | 720 |
| cttgcaatgt ttgcccattt tagggacatg agtaggctga agtttgttca gtgtggactt | 780 |
| cagaggcagc acacaaacag caagctttgc tctagactgg aattcgtcga cgagctccct | 840 |
| atagtgagtc gtattagagg ccgactgacc cggtacccgg ggatcttgct accagtggaa | 900 |
| cagccactaa ggattctgca gtgagagcag agggccagct aagtggtact ctcccagaga | 960 |
| ctgtctgact cacgccaccc cctccacctt ggacacagga cgctgtggtt tctgagccag | 1020 |
| gtacaatgac tcctttcggt aagtgcagtg gaagctgtac actgcccagg caaagcgtcc | 1080 |
| gggcagcgta ggcgggcgac tcagatccca gccagtggac ttagccctg tttgctcctc | 1140 |
| cgataactgg ggtgaccttg gttaatattc accagcagcc tccccgttg ccctctgga | 1200 |
| tccactgctt aaatacggac gaggacaggg cctgtctcc tcagcttcag gcaccaccac | 1260 |
| tgacctggga cagtgaatgt cccctgatc tgcggccgtg actctcttaa ggtagccttg | 1320 |
| cagaagttgg tcgtgaggca ctgggcaggt aagtatcaag gttacaagac aggtttaagg | 1380 |

```
agaccaatag aaactgggct tgtcgagaca gagaagactc ttgcgtttct gataggcacc  1440
tattggtctt actgacatcc actttgcctt tctctccaca ggtgtccact cccagttcaa  1500
ttacagctct taaggctaga gtacttaata cgactcacta taggctagcc tcgacctcga  1560
gatgattcct ggtaaccgaa tgctgatggt cgttttatta tgccaagtcc tgctaggagg  1620
cgcgagccat gctagtttga tacctgagac ggggaagaaa aaagtcgccg agattcaggg  1680
ccacgcggga ggacgccgct cagggcagag ccatgagctc ctgcgggact tcgaggcgac  1740
acttctgcag atgtttgggc tgcgccgccg cccgcagcct agcaagagtg ccgtcattcc  1800
ggactacatg cgggatcttt accgcttca gtctggggag gaggaggaag agcagatcca  1860
cagcactggt cttgagtatc ctgagcgccc ggccagccgg ccaacaccg tgaggagctt  1920 ccaccacgaa gaacatctgg agaacatccc agggaccagt gaaaactctg cttttcgttt  1980
cctctttaac ctcagcagca tccctgagaa cgaggtgatc tcctctgcag agcttcggct  2040
cttccgggag caggtggacc agggccctga ttgggaaagg ggcttccacc gtataaacat  2100
ttatgaggtt atgaagcccc cagcagaagt ggtgcctggg cacctcatca cacgactact  2160
ggacacgaga ctggtccacc acaatgtgac acggtgggaa acttttgatg tgagccctgc  2220
ggtccttcgc tggacccggg agaagcagcc aaactatggg ctagccattg aggtgactca  2280
cctccatcag actcggaccc accagggcca gcatgtcagg attagccgat cgttacctca  2340
agggagtggg aattgggccc agctccggcc cctcctggtc acctttggcc atgatggccg  2400
gggccatgcc ttgacccgac gccggagggc caagcgtagc cctaagcatc actcacagcg  2460
ggccaggaag aagaataaga actgccggcg ccactcgctc tatgtggact tcagcgatgt  2520
gggctggaat gactggattg tggccccacc aggctaccag gccttctact gccatgggga  2580 ctgcccctt ccactggctg accacctcaa ctcaaccaac catgccattg tgcagaccct  2640
ggtcaattct gtcaattcca gtatccccaa agcctgttgt gtgccactg aactgagtgc  2700 catctccatg ctgtacctgg atgagtatga taaggtggta ctgaaaaatt atcaggagat  2760
ggtagtagag ggatgtgggt gccgctgaac gcgtgatatc ggatcccggc cggcggccgc  2820
ttccctttag tgagggttaa tgcttcgagc agacatgata agatacattg atgagtttgg  2880
acaaaccaca actagaatgc agtgaaaaaa atgctttatt tgtgaaattt gtgatgctat  2940
tgctttattt gtaaccatta taagctgcaa taaacaagtt aacaacaaca attgcattca  3000
ttttatgttt caggttcagg gggagatgtg ggaggttttt taaagcaagt aaaacctcta  3060
caaatgtggt aaaatccgat aagggactag agcatggcta cgtagataag tagcatggcg  3120
ggttaatcat taactacaag gaaccctag tgatggagtt ggccactccc tctctgcgcg  3180
ctcgctcgct cactgaggcc gggcgaccaa aggtcgcccg acgcccgggc tttgcccggg  3240
cggcctcagt gagcgagcga gcgcgccagc tggcgtaata gcgaagaggc ccgcaccgat  3300
```

ADENO-ASSOCIATED VIRAL VECTORS FOR THE GENE THERAPY OF METABOLIC DISEASES

SEQUENCE LISTING SUBMISSION VIA EFS-WEB

A computer readable text file, entitled "Sequence-Listing.txt", created on or about Mar. 15, 2017, with a file size of about 22 KB contains the sequence listing for this application and is hereby incorporated by reference in its entirety

TECHNICAL FIELD

The invention relates to the field of gene therapy and, more particularly, to methods for the treatment of metabolic diseases such as obesity, insulin resistance, type 2 diabetes, liver cirrhosis and non-alcoholic fatty liver disease/non-alcoholic steatohepatitis (NAFLD/NASH) by the use of adeno-associated viral vectors.

BACKGROUND OF THE INVENTION

The current epidemic of obesity and the metabolic syndrome is a global health problem. Adipose tissue has a vital role in regulating energy homeostasis, and the interest in the complex biology of adipose tissue is increasing greatly.

There are two principal types of adipose tissue: white adipose tissue (WAT) and brown adipose tissue (BAT) but recent studies have shown the presence of an intermediate phenotype, the beige cells, which also are oxidative. WAT has the main function to store energy as triglycerides during caloric excess. During weight gain, WAT undergoes expansion, either through increasing the number of adipocytes, or by enlargement of existing adipocytes, so-called hypertrophic obesity. Hypertrophic adipose tissue expansion is tightly correlated with disorders of the metabolic syndrome such as insulin resistance, type 2 diabetes and systemic low-grade inflammation.

In last few years, a third, distinct type of adipocyte has been identified, so-called beige or brite (brown-in-white) adipocytes. These cells reside as a separate population within white fat depots, probably have a white adipocyte stem cell origin and show a white adipocyte phenotype under basal conditions. A study has demonstrated that recruitment of beige/brite cells after chronic cold exposure also lead to reduced body fat, demonstrating potential important anti-obesity effects of these cells in humans.

The incidence of obesity has increased dramatically during the last decades to reach epidemic proportions. It is estimated that over 500 million individuals are obese. Obesity per se increases the risk of mortality and has been long strongly associated with insulin resistance and type 2 diabetes.

Diet and exercise are the mainstay treatments for obesity, but an increasing number of patients also require pharmacotherapeutic intervention to decrease and maintain body weight. However, pharmacotherapy does not induce involuntarily nor substantial weight loss and, additionally, anti-obesity drugs often display important side effects due to their systemic actions.

In addition, the growing incidence of obesity in the population as a whole has made fatty liver disease and its complications a leading public health issue. Non-alcoholic fatty liver disease (NAFLD) is characterized by an aberrant lipid storage in hepatocytes. It is related to insulin resistance and the metabolic syndrome and may respond to treatments originally developed for other insulin-resistant states (e.g. diabetes mellitus type 2) such as weight loss, metformin and thiazolidinediones. NAFLD can progress to NASH (non-alcoholic steatohepatitis) which is characterized by the appearance of necroinflammation in the liver. Non-alcoholic steatohepatitis (NASH) is the most extreme form of NAFLD, and is regarded as a major cause of cirrhosis of the liver of unknown cause.

Liver transplantation is the only curative option for patients with advanced liver cirrhosis. This procedure can only be applied to a minority of patients due to the presence of surgical contraindications and organ scarcity.

Several authors have disclosed recombinant adeno-associated viruses potentially useful in the treatment of diabetes, obesity and related complications. For example, Orellana-Gavaldà J M et al. (Orellana-Gavaldà J M et al. 2011. Hepatology, 53(3): 821-32) used adeno-associated viruses to mediate long-term hepatic gene transfer of CPT1A or its permanently active mutant form CPT1AM, to high-fat-diet-treated and genetically obese mice and showed that CPT1A- and, to a greater extent, CPT1AM-expressing mice were protected against obesity-induced weight gain, hepatic steatosis, diabetes, and obesity-induced insulin resistance.

Doege H. et al. (Doege H. et al. 2008. J Biol Chem, 283(32): 22186-92) disclosed an adeno-associated virus-mediated RNA interference technique to knock down the expression of hepatic fatty acid transport protein 5 in vivo prior to or after establishing NAFLD in mice. This approach protected mice from diet-induced NAFLD and was able to reverse already established NAFLD, resulting in significantly improved whole-body glucose homeostasis.

Accordingly, there is an urgent need for alternative approaches to prevent and combat the current obesity epidemic and metabolic disorders associated.

SUMMARY OF THE INVENTION

In a first aspect, the invention relates to an adeno-associated viral vector comprising a recombinant viral genome wherein said recombinant viral genome comprises an expression cassette comprising a transcriptional regulatory region operatively linked to a nucleotide sequence encoding BMP4 or a functionally equivalent variant thereof with the proviso that when the expression cassette comprises a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal, and said expression cassette is flanked by AAV2 ITRs, then the serotype of the adeno-associated viral vector is not AAV2.

In a second aspect, the invention relates to a pharmaceutical composition comprising an adeno-associated viral vector according to the first aspect of the invention.

In a third aspect, the invention relates to an associated viral vector according to the first aspect of the invention or a pharmaceutical composition according to the second aspect of the invention for use in medicine.

In a fourth aspect, the invention relates to an adeno-associated viral vector comprising a recombinant viral genome wherein said recombinant viral genome comprises an expression cassette comprising a transcriptional regulatory region operatively linked to a nucleotide sequence encoding BMP4 or a functionally equivalent variant thereof or a pharmaceutical composition comprising said viral vector for use in the treatment and/or prevention of a disease selected from the group consisting of obesity, insulin resistance, type 2 diabetes, liver cirrhosis and non-alcoholic fatty liver disease (NAFLD)/non-alcoholic steatohepatitis (NASH).

In a fifth aspect, the invention relates to a polynucleotide comprising an expression cassette flanked by adeno-associated virus ITRs wherein said expression cassette comprises a transcriptional regulatory region operatively linked to a nucleotide sequence encoding BMP4 or a functionally equivalent variant thereof with the proviso that the expression cassette is not an expression cassette comprising a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal.

In yet another aspect, the invention relates to a vector or a plasmid comprising a polynucleotide of the invention.

In yet another aspect, the invention relates to a method for obtaining an adeno-associated viral vector comprising the steps of:
(i) providing a cell comprising a polynucleotide of the invention, AAV Cap proteins, AAV Rep proteins and, optionally, viral proteins upon which AAV is dependent for replication,
(ii) maintaining the cell under conditions adequate for assembly of the AAV and
(iii) purifying the adeno-associated viral vector produced by the cell.

DESCRIPTION OF THE INVENTION

Figure 1:
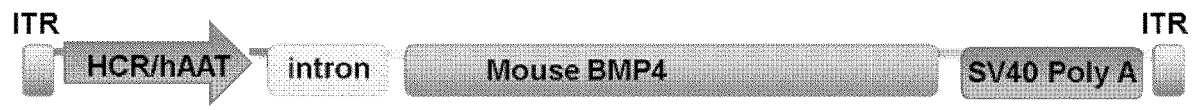
FIG. 1. Schematic view of ITR hAAT mBMP4 ITR construct. The expression cassette of the invention is formed by a transcriptional regulatory region comprising the hepatic control region enhancer and the human alpha 1-antitrypsin promoter (HCR/hAAT P) operatively linked to mouse BMP4 cDNA (mBMP4) and further comprising the SV40 polyadenilation signal (SV40polyA). Said expression cassette is flanked by adeno-associated terminal repeats (5' AAV ITR and 3' AAV ITR). bp, base pairs.

The authors of the present invention have observed that the administration to adult mice challenged with high fat diet of an adeno-associated viral vector encoding BMP4, wherein the polynucleotide encoding BMP4 is under the control of a liver-specific promoter, produces an improvement in the metabolic profile of said mice compared to their controls, such as having reduced body weight gain (Example 1), being more glucose tolerant and having lower circulating insulin levels (Example 2), being more insulin sensitive (Example 3), and having reduced adipocyte size (Example 6). Furthermore, the subcutaneous adipose cells assumed a beige/brown phenotype (Example 8) demonstrating that these mice have a healthier, more oxidative white adipose tissue. These findings suggest that BMP4 gene transfer with AAV vectors is a potential preventive and/or therapeutic option for patients with obesity, insulin resistance or type 2 diabetes. The authors of the invention have also found that fat in the liver and associated fibrosis were also reduced in high fat-fed mice treated with adeno-associated viral vectors encoding BMP4 (Examples 10 and 11) thus suggesting that BMP4 gene transfer with such vectors is also a potential preventive/therapeutic option for those patients having NAFDL/NASH and advanced liver cirrhosis whom cannot be offered liver transplant or who deteriorate on the waiting list for transplantation.

Adeno-Associated Viral Vectors of the Invention

In a first aspect, the invention relates to an adeno-associated viral (AAV) vector comprising a recombinant viral genome wherein said recombinant viral genome comprises an expression cassette comprising a transcriptional regulatory region operatively linked to a nucleotide sequence encoding BMP4 or a functionally equivalent variant thereof with the proviso that when the expression cassette comprises a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal, and said expression cassette is flanked by AAV2 ITRs, then the serotype of the adeno-associated viral vector is not AAV2.

The terms "adeno-associated viral vector", "AAV vector", "adeno-associated virus", "AAV virus", "AAV virion", "AAV viral particle" and "AAV particle", as used interchangeably herein, refer to a viral particle composed of at least one AAV capsid protein (preferably by all of the capsid proteins of a particular AAV serotype) and an encapsidated recombinant viral genome. The particle comprises a recombinant viral genome having a heterologous polynucleotide (i.e. a nucleotide sequence encoding BMP4 or a functionally equivalent variant thereof) and a transcriptional regulatory region that at least comprises a promoter to be delivered to a mammalian cell flanked by the AAV inverted terminal repeats and it is typically referred to as an "AAV vector particle" or "AAV vector".

AAV refers to viruses belonging to the genus Dependovirus of the Parvoviridae family. The AAV genome is approximately 4.7 kilobases long and is composed of linear single-stranded deoxyribonucleic acid (ssDNA) which may be either positive- or negative-sensed. The genome comprises inverted terminal repeats (ITRs) at both ends of the DNA strand, and two open reading frames (ORFs): rep and cap. The rep frame is made of four overlapping genes encoding non-structural replication (Rep) proteins required for the AAV life cycle. The cap frame contains overlapping nucleotide sequences of structural VP capsid proteins: VP1, VP2 and VP3, which interact together to form a capsid of an icosahedral symmetry. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the rep genes (i.e. Rep78 and Rep52) are expressed from the P5 promoter and the P19 promoter, respectively, and both Rep proteins have a function in the replication of the viral genome. A splicing event in the rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The AAV vector of the invention typically lacks rep and cap frames. Such AAV vectors can be replicated and packaged into infectious viral particles when present in a host cell that has been transfected with a vector encoding and expressing rep and cap gene products (i.e. AAV Rep and Cap proteins), and wherein the host cell has been transfected with a vector which encodes and expresses a protein from the adenovirus open reading frame E4orf6. In a more preferred embodiment, the AAV recombinant genome of the AAV vector of the invention lacks the rep open reading frame and/or the cap open reading frame.

The AAV vector of the invention comprises a capsid from any serotype. In general, the AAV serotypes have genomic sequences of significant homology at the amino acid and the nucleic acid levels, provide an identical set of genetic functions, and replicate and assemble through practically identical mechanisms. In particular, the AAV of the present invention may belong to the serotype 1 of AAV (AAV1), AAV2, AAV3 (including types 3A and 3B), AAV4, AAV5, AAV6, AAV7, AAV8, AAV9, AAV10, AAVrh10, AAV11, avian AAV, bovine AAV, canine AAV, equine AAV, ovine AAV, and any other AAV not known or later discovered. Examples of the sequences of the genome of the different AAV serotypes may be found in the literature or in public databases such as GenBank. For example, GenBank accession numbers NC_001401.2 (AAV2), NC_001829.1 (AAV4), NC_006152.1 (AAV5), AF028704.1 (AAV6), NC_006260.1 (AAV7), NC_006261.1 (AAV8), AX753250.1 (AAV9) and AX753362.1 (AAV10). In a preferred embodiment, the adeno-associated viral vector of the invention comprises a capsid derived from a serotype selected from the group consisting of the AAV2, AAV5, AAV7, AAV8, AAV9, AAV10 and AAVrh10 serotypes. In a more preferred embodiment, the serotype of the AAV is AAV8.

If the viral vector comprises sequences encoding the capsid proteins, these may be modified so as to comprise an exogenous sequence to direct the AAV to a particular cell type or types, or to increase the efficiency of delivery of the targeted vector to a cell, or to facilitate purification or detection of the AAV, or to reduce the host response.

The expression "recombinant viral genome", as used herein, refers to an AAV genome in which at least one extraneous expression cassette polynucleotide is inserted into the naturally occurring AAV genome. The genome of the AAV according to the invention typically comprises the cis-acting 5' and 3' inverted terminal repeat sequences (ITRs) and an expression cassette.

The term "adeno-associated virus ITRs" or "AAV ITRs", as used herein, refers to the inverted terminal repeats present at both ends of the DNA strand of the genome of an adeno-associated virus. The ITR sequences are required for efficient multiplication of the AAV genome. Another property of these sequences is their ability to form a hairpin. This characteristic contributes to its self-priming which allows the primase-independent synthesis of the second DNA strand. The ITRs were also shown to be required for both integration of the wild-type AAV DNA into the host cell genome (i.e. 19$^{th}$ chromosome in humans) and rescue from it, as well as for efficient encapsidation of the AAV DNA combined with generation of a fully assembled, deoxyribonuclease-resistant AAV particles. The ITR sequences are about 145 bp in length. Preferably, substantially the entire sequences encoding the ITRs are used in the molecule, although some degree of minor modification of these sequences is permissible. A wild-type sequence may be altered by insertion, deletion, truncation or missense mutation, as long as the ITR mediates the desired functions, e.g. replication, nicking, virus packaging, integration, and/or provirus rescue, and the like. Procedures for modifying these ITR sequences are known in the art (Brown T, "Gene Cloning", Chapman & Hall, London, GB, 1995; Watson R, et al., "Recombinant DNA", 2nd Ed. Scientific American Books, New York, N.Y., US, 1992; Alberts B, et al., "Molecular Biology of the Cell", Garland Publishing Inc., New York, N.Y., US, 2008; Innis M, et al., Eds., "PCR Protocols. A Guide to Methods and Applications", Academic Press Inc., San Diego, Calif., US, 1990; and Schleef M, Ed., "Plasmid for Therapy and Vaccination", Wiley-VCH Verlag GmbH, Weinheim, Del., 2001). The ITR may be from any AAV, including but not limited to serotypes 1, 2, 3, 4, 5, 6, 7, 8, 9, 10, 11 or 12 or any other AAV known or later discovered. The AAV comprises two ITRs, which may be the same or different. Further, the two AAV ITRs can be from the same AAV serotype as the AAV capsid, or can be different. In a preferred embodiment, the 5' and 3' AAV ITRs derive from AAV1, AAV2, AAV4, AAV5, AAV7, AAV9 and/or AAV8. Preferably ITRs are from AAV2 or AAV8, being AAV2 the most preferred. In one embodiment, the AAV2 ITRs are selected to generate a pseudotyped AAV (i.e. an AAV having a capsid and ITRs derived from different serotypes). In a more preferred embodiment, the 5' AAV ITR has a sequence SEQ ID NO: 2. In a more preferred embodiment the 3' AAV ITR has a sequence SEQ ID NO: 3.

In another embodiment, the serotype of the adeno-associated viral vector is not AAV2.

The term "expression cassette", as used herein, refers to a nucleic acid construct, generated recombinantly or synthetically, with a series of specified nucleic acid elements, which permit transcription of a particular nucleic acid in a target cell. The expression cassette of the recombinant viral genome of the AAV vector of the invention comprises a transcriptional regulatory region operatively linked to a nucleotide sequence encoding BMP4 or a functionally equivalent variant thereof.

The term "transcriptional regulatory region", as used herein, refers to a nucleic acid fragment capable of regulating the expression of one or more genes. The transcriptional regulatory region of the invention includes a promoter and, optionally, an enhancer.

In an embodiment, the transcriptional regulatory region comprises a promoter.

The term "promoter", as used herein, refers to a nucleic acid fragment that functions to control the transcription of one or more polynucleotides, located upstream the polynucleotide sequence(s), and which is structurally identified by the presence of a binding site for DNA-dependent RNA polymerase, transcription initiation sites, and any other DNA sequences including, but not limited to, transcription factor binding sites, repressor, and activator protein binding sites, and any other sequences of nucleotides known in the art to act directly or indirectly to regulate the amount of transcription from the promoter. Any kind of promoters may be used in the invention including inducible promoters, constitutive promoters and tissue-specific promoters.

In an embodiment, the promoter is an inducible promoter. The expression "inducible promoter", as used herein, refers to a promoter that is physiologically or developmentally regulated, e.g. by the application of a chemical inducer. For example, it can be a tetracycline-inducible promoter, a mifepristone (RU-486)-inducible promoter and the like.

In another embodiment, the promoter is a constitutive promoter. The expression "constitutive promoter", as used herein, refers to a promoter whose activity is maintained at a relatively constant level in all cells of an organism, or during most developmental stages, with little or no regard to cell environmental conditions. In a preferred embodiment, the transcriptional regulatory region allows constitutive expression of BMP4. Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1a promoter (Boshart M, et al., Cell 1985; 41:521-530). Preferably, the constitutive promoter is suitable for expression of BMP4 in liver and include, without limitation, a promoter of hypoxanthine phosphoribosyl transferase (HPTR), a promoter of the adenosine deaminase, a promoter of the pyruvate kinase, a promoter of β-actin, an elongation factor 1 alpha (EF1) promoter, a phosphoglycerate kinase (PGK) promoter, a ubiquitin (Ubc) promoter, an albumin promoter, and other constitutive promoters. Exemplary viral promoters which function constitutively in eukaryotic cells include, for example, the SV40 early promoter region (Bernoist and Chambon, 1981, Nature 290:304-310), the promoter contained in the 3' long terminal repeat of Rous sarcoma virus (Yamamoto et al., 1980, Cell 22:787-797), or the herpes thymidine kinase promoter (Wagner et al., 1981, Proc. Natl. Acad. Sci. U.S.A. 78:1441-1445). In an embodiment, the constitutive promoter is the β-actin promoter. The β-actin promoter may be derived from any mammal, including human and rodent, or bird, including chicken. Preferably, a chicken β-actin promoter is used.

In another embodiment, the promoter may be a tissue-specific promoter. A "tissue-specific" promoter is only active in specific types of differentiated cells or tissues. Typically, the downstream gene in a tissue-specific promoter is one which is active to a much higher degree in the tissue(s) for which it is specific than in any other. In this case there may be little or substantially no activity of the promoter in any tissue other than the one(s) for which it is specific.

Preferably, the promoter is a liver-specific promoter. The term "liver-specific promoter", as used herein, refers to a nucleic acid sequence that serves as a promoter (i.e. regulates expression of a selected nucleic acid sequence operably linked to the promoter), and which affects the expression of a selected nucleic acid sequence in specific tissue cells, such as hepatocytes. Typically, a liver-specific promoter is more active in liver as compared to its activity in any other tissue in the body. The liver-specific promoter can be constitutive or inducible. Suitable liver-specific promoters include, without limitation, an [alpha]1-anti-trypsin (AAT) promoter, a thyroid hormone-binding globulin promoter, an alpha fetoprotein promoter, an alcohol dehydrogenase promoter, the factor VIII (FVIII) promoter, a HBV basic core promoter (BCP) and PreS2 promoter, an albumin promoter, a −460 to 73 pb phosphoenol pyruvate carboxykinase (PEPCK) promoter, a thyroxin-binding globulin (TBG) promoter, an Hepatic Control Region (HCR)-ApoCII hybrid promoter, an HCR-hAAT hybrid promoter, an AAT promoter combined with the mouse albumin gene enhancer (Ealb) element, an apolipoprotein E promoter, a low density lipoprotein promoter, a pyruvate kinase promoter, a lecithin-cholesterol acyl transferase (LCAT) promoter, an apolipoprotein H (ApoH) promoter, the transferrin promoter, a transthyretin promoter, an alpha-fibrinogen and beta-fibrinogen promoters, an alpha 1-antichymotrypsin promoter, an alpha 2-HS glycoprotein promoter, an haptoglobin promoter, a ceruloplasmin promoter, a plasminogen promoter, promoters of the complement proteins (CIq, CIr, C2, C3, C4, C5, C6, C8, C9, complement Factor I and Factor H), C3 complement activator and the [alpha]-acid glycoprotein promoter. Additional tissue-specific promoters may be found in the Tissue-Specific Promoter Database, TiProD (Nucleic Acids Research, J4:D104-D107 (2006)). In a more preferred embodiment, the liver-specific promoter is selected from the group consisting of albumin promoter, phosphoenol pyruvate carboxykinase (PEPCK) promoter and alpha 1-antitrypsin promoter; more preferably alpha 1-antitrypsin promoter; even more preferably human alpha 1-antitrypsin promoter.

In another embodiment, the promoter is a skeletal muscle-specific promoter. The term "skeletal muscle-specific promoter", as used herein, refers to a nucleic acid sequence that serves as a promoter (i.e. regulates expression of a selected nucleic acid sequence operably linked to the promoter), and which affects the expression of a selected nucleic acid sequence in specific tissue cells of skeletal muscle. Examples of skeletal muscle-specific promoters include, without limitation, myosin light chain promoter (MLC) and the muscle creatine kinase promoter (MCK).

In another embodiment, the transcriptional regulatory region further comprises an enhancer operatively linked to the promoter.

The term "enhancer", as used herein, refers to a DNA sequence element to which transcription factors bind to increase gene transcription. Examples of enhancers may be, without limitation, RSV enhancer, CMV enhancer, HCR enhancer, etc. In a preferred embodiment, the enhancer is a liver-specific enhancer, more preferably a hepatic control region enhancer (HCR).

If the promoter is liver-specific, then the enhancer need not be liver-specific as well. Alternatively, the transcriptional regulatory region may comprise a liver-specific promoter and a liver-specific enhancer.

In a preferred embodiment, the liver-specific transcriptional-regulatory region of the AAV vector according to the invention comprises the liver-specific enhancer HCR (hepatic control region enhancer) and the liver-specific promoter alpha 1-antitrypsin promoter, preferably the human alpha 1-antitrypsin promoter. In a more preferred embodiment, the liver-specific transcriptional-regulatory region has the sequence SEQ ID NO: 4.

Although any tissue-specific transcriptional regulatory region may be used in the AAV vector of the present invention, in a particular embodiment the transcriptional regulatory region is not an adipose tissue-specific transcriptional regulatory region.

The expression "adipose tissue-specific transcriptional regulatory region", as used herein, relates to a nucleic acid sequence that serves as a promoter (i.e. regulates expression of a selected nucleic acid sequence operably linked to the promoter), and which affects the expression of a selected nucleic acid sequence in specific tissue cells such as adipocytes. The adipose tissue-specific transcriptional regulatory region can be constitutive or inducible. Exemplary adipose tissue-specific promoters are, without limitation, the adipocyte protein 2 (aP2, also known as fatty acid binding protein 4 (FABP4), the PPARγ promoter, the adiponectin promoter, the phosphoenolpyruvate carboxykinase (PEPCK) promoter, the promoter derived from human aromatase cytochrome p450 (p450arom), or the Foxa-2 promoter. The adipose tissue-specific enhancer may be, without limitation, the adipose-specific aP2 enhancer and the adipose-specific UCP1 enhancer.

The transcriptional regulatory region of the expression cassette is operatively linked to a nucleotide sequence encoding BMP4 or a functionally equivalent variant thereof.

The expression "operatively linked", as used herein, refers to the functional relation and location of a promoter sequence with respect to a polynucleotide of interest (e.g. a promoter or enhancer is operably linked to a coding sequence if it affects the transcription of the sequence). Generally, a promoter operatively linked is contiguous to the sequence of interest. However, an enhancer does not have to be contiguous to the sequence of interest to control its expression. In a preferred embodiment, the promoter and the nucleotide sequence encoding BMP4 or a functionally equivalent variant thereof are separated by an intron, preferably said intron has the sequence SEQ ID NO: 5.

The term "nucleotide sequence", is used herein interchangeably with "polynucleotide", and relates to any polymeric form of nucleotides of any length. Said nucleotide sequence encodes BMP4 protein or a functionally equivalent variant thereof.

The term "BMP4", as used herein, is used interchangeably with the term "bone morphogenetic protein 4" and relates to a member of the bone morphogenetic protein family which is part of the transforming growth factor-beta superfamily. The bone morphogenetic protein family has central roles in regulating stem cell development, particularly in skeletal development as the name indicates. In addition to skeletal development, BMP4 also has central roles in committing stem cells/precursor cells to the white and brown adipocyte lineages. The invention contemplates the use of polynucleotides encoding BMP4 from any animal species. Suitable BMP4 molecules useful for the invention include, without limitation, human BMP4, which corresponds to the sequence of the NCBI database with accession number NP_001193.2 dated 3 May 2014, or to the sequence of the NCBI database with accession number NP_570911.2 dated 27 Apr. 2014, or to the sequence of the NCBI database with accession number NP_570912.2 dated 27 Apr. 2014, or to the predicted sequence of the NCBI database corresponding to isoform X1 having accession number XP_005268072.1 dated 3 Feb. 2014. The invention also contemplates the use of BMP4 from different animal species, such as, without limitation, mouse BMP4, which corresponds to the sequence of the NCBI database with accession number NP_031580.2 dated 27 Apr. 2014; rat BMP4, which corresponds to the sequence of the NCBI database with accession number NP_036959.2 dated 10 Aug. 2014; chicken BMP4, which corresponds to the sequence of the NCBI database with accession number NP_990568.3 dated 4 May 2014; bovine BMP4 which corresponds to the sequence of the NCBI database with accession number NP_001039342.1 dated 26 Jan. 2014; pig BMP4 which corresponds to the sequence of the NCBI database with accession number NP_001094501.1 dated 4 May 2014; rabbit BMP4 which corresponds to the sequence of the NCBI database with accession number NP_001182652.1 dated 12 Mar. 2014; sheep BMP4 which corresponds to the sequence of the NCBI database with accession number NP_001103747.1 dated 18 Apr. 2013; goat BMP4 which corresponds to the sequence of the NCBI database with accession number NP_001272575.1 dated 29 Dec. 2013.

In a preferred embodiment, BMP4 is selected from the group consisting of human BMP4 and mouse BMP4, preferably is from human origin.

The skilled person will appreciate that BMP4 is synthesized as an inactive preprotein containing a signal peptide region, a pre-peptide region and a mature chain. The signal peptide directs the protein to the secretory pathway. Dimerization of the BMP4 preprotein occurs by forming an intermolecular disulphide bond. Then, it is cleaved post-translationally by members of the subtilisin-like proprotein convertase family, to obtain an active carboxyl-terminal mature BMP4 protein dimer, which is then secreted outside the cell. Thus, the nucleotide sequence present in the viral vector of the invention may encode for the full-length precursor form, which should then be processed by the target cell machinery. Alternatively, it is also possible to include a polynucleotide encoding the propeptide fused to a heterologous signal sequence. The expression "signal sequence", as used herein, refers to a DNA sequence at the 5' end of a structural gene which is transcribed and translated along with the gene. The leader usually results in the protein having an N-terminal peptide extension sometimes called a pro-sequence. For proteins destined for either secretion to the extracellular medium or the membrane, this signal sequence directs the protein into endoplasmic reticulum from which it is discharged to the appropriate destination. The leader sequence normally is encoded by the desired nucleic acid, synthetically derived or isolated from a different gene sequence. Heterologous sequences suitable as signal sequences for promoting secretion of the polynucleotide of the invention include the signal sequences of gelsolin, albumin, fibrinogen, among others, and the signal peptides from tissue plasminogen activator, insulin, and neuron growth factor (NGF).

The skilled person will also appreciate that, as long as the length of the viral genome does not exceed the packaging size limit of the viral capsid, the viral genome of the AAV vector of the invention may comprise part or all of the genomic sequence encoding BMP4, in which case, the coding region of BMP4 will be interrupted by intronic regions.

The invention also contemplates recombinant viral genomes which comprise nucleotide sequences encoding BMP4 variants and fragments known in the art. Thus, the invention should be construed to include DNA encoding functional equivalent variants of BMP4.

The term "functional equivalent variant", as used herein, relates to any polypeptide substantially homologous to the sequences of BMP4 defined above and that preserves the biological activity of BMP4. The sequence of such functional equivalent variants can be obtained from the sequence of BMP4 as defined above by means of insertion, substitution or deletion of one or more amino acids and which substantially preserves the biological activity of BMP4. Methods for determining whether a variant preserves the biological activity of the native BMP4 are widely known to the skilled person and include any of the assays used in the experimental part of said application. Particularly, functionally equivalent variants of BMP4 encompassed by the present invention have at least one of the functions of BMP4 such as, without limitation:

the ability to reduce body weight gain as disclosed in Example 1 of the present invention. A method suitable for determining the reduction in body weight is detailed in the Materials and Methods section of the present invention.

the ability to reduce circulating insulin levels and induce glucose tolerance as disclosed in Example 2 of the present invention. A method suitable for determining said parameters is detailed in the Materials and Methods section of the present invention.

the ability to induce insulin sensitivity as disclosed in Example 3 of the present invention. A method suitable for determining said parameter is detailed in the Materials and Methods section of the present invention.

the ability to reduce fat mass and increase lean tissue as disclosed in Example 4 of the present invention. A method for determining said parameters is detailed in the Materials and Methods section of the present invention.

the ability to reduce eipidymal, subcutaneous and/or mesenteric fat depots as disclosed in Example 5 of the present invention. A method for determining said parameter is detailed in the Materials and Methods section of the present invention.

the ability to reduce adipocyte size as disclosed in Example 6 of the present invention. A method suitable for determining said parameter is detailed in the Materials and Methods section of the present invention.

the ability to induce a beige/brown phenotype in subcutaneous adipose cells as disclosed in Example 8 of the present invention. A method suitable for determining said activity is detailed in the Materials and Methods section of the present invention.

the ability to reduce fat accumulation in liver as disclosed in Example 11 of the present invention. A method suitable for determining said fat accumulation is detailed in the Materials and Methods section of the present invention.

the ability to reduce liver fibrosis as disclosed in Example 10 of the present invention. A method suitable for determining liver fibrosis is detailed in the Materials and Methods section of the present invention.

the ability to improve oxidative phenotype in skeletal muscle as disclosed in Example 12 of the present invention. A method suitable for determining said activity is detailed in the Materials and Methods section of the present invention.

In a preferred embodiment, a polypeptide is considered a functionally equivalent variant of BMP4 if it shows an ability in any of the functions detailed below that is at least 10%, 20%, 30%, 40%, 50%, 60%, 70%, 80%, 90% or 100% of the ability of the BMP4 of any of the sequences referred above, preferably of the sequence of the NCBI database with accession number NP_031580.2 dated 27 Apr. 2014, more preferably of the sequence SEQ ID NO: 7.

The functionally equivalent variants of BMP4 are polypeptides substantially homologous to the native BMP4. The expression "substantially homologous", relates to a protein sequence when said protein sequence has a degree of identity with respect to the BMP4 sequences described above of at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99%. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)], though other similar algorithms can also be used. BLAST and BLAST 2.0 are used, with the parameters described herein, to determine percent sequence identity. Software for performing BLAST analyses is publicly available through the National Center for Biotechnology Information.

Functionally equivalent variants of BMP4 may be obtained by replacing nucleotides within the polynucleotide accounting for codon preference in the host cell that is to be used to produce the BMP4. Such "codon optimization" can be determined via computer algorithms which incorporate codon frequency tables such as "Human high.cod" for codon preference as provided by the University of Wisconsin Package Version 9.0, Genetics Computer Group, Madison, Wis.

Functionally equivalent variants of BMP4 may be generated by making conservative amino acid changes and testing the resulting variant in one of the functional assays described above or another functional assay known in the art. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having eamide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The expression cassette of the AAV vector of the invention comprises a nucleotide sequence encoding BMP4 or a functionally equivalent variant thereof. In an embodiment, said nucleotide sequence is the nucleotide sequence encoding mouse BMP4, which corresponds to the sequence of the NCBI database with accession number NM_007554.2 dated 27 Apr. 2014, more preferably it is SEQ ID NO: 6. In a preferred embodiment, the nucleotide sequence is a variant of the nucleotide sequence encoding mouse BMP4, preferably is SEQ ID NO: 7. In a more preferred embodiment, said nucleotide sequence is the nucleotide sequence encoding human BMP4 SEQ ID NO: 8. In a more preferred embodiment, the nucleotide sequence is a variant of the nucleotide sequence encoding human BMP4.

The expression cassette which forms part of the AAV of the invention further comprises expression control sequences including, but not limited to, appropriate transcription sequences (i.e. initiation, termination, promoter, and enhancer), efficient RNA processing signals (e.g. splicing and polyadenylation (polyA) signals), sequences that stabilize cytoplasmic mRNA, sequences that enhance translation efficiency (i.e. Kozak consensus sequence), sequences that enhance protein stability, and when desired, sequences that enhance secretion of the encoded product. A great number of expression control sequences are known in the art and may be utilized according to the present invention.

In another embodiment, the expression cassette which forms part of the AAV vector of the invention further comprises a post-transcriptional regulatory region. The term "post-transcriptional regulatory region", as used herein, refers to any polynucleotide that facilitates the expression, stabilization, or localization of the sequences contained in the cassette or the resulting gene product. The post-transcriptional regulatory region may be, without limitation, the Woodchuck Hepatitis Virus post-transcriptional region (WPRE).

In another embodiment, the expression cassette further comprises a polyadenylation signal.

The term "polyadenylation signal", as used herein, relates to a nucleic acid sequence that mediates the attachment of a polyadenine stretch to the 3' terminus of the mRNA. Suitable polyadenylation signals include, without limitation, the SV40 early polyadenylation signal, the SV40 late polyadenylation signal, the HSV thymidine kinase polyadenylation signal, the protamine gene polyadenylation signal, the adenovirus 5 EIb polyadenylation signal, the bovine growth hormone polyadenylation signal, the human variant growth hormone polyadenylation signal and the like.

In a particular embodiment, the polyadenylation signal is SV40polyA or functional variants and fragments thereof, preferably SV40polyA. In a more preferred embodiment, the nucleotide sequence of SV40poly A is SEQ ID NO: 9.

In a preferred embodiment, the adeno-associated viral vector of the invention comprises a recombinant viral genome comprising a nucleotide sequence containing an expression cassette comprising in the 5' to 3' direction, (i) a 5' AAV2 ITR, (ii) a hepatic control region (HCR) enhancer, (iii) a human alpha 1-antitrypsin promoter (hAAT), (iv) the mouse BMP4 cDNA or a functionally equivalent variant thereof, (v) the SV40 polyadenilation signal (SV40polyA), and (vi) a 3' AAV2 ITR. Those skilled in the art will appreciate that the vector genome can comprise other sequences (e.g. intervening sequences between the sequences specifically described above). In an embodiment, said nucleotide sequence is SEQ ID NO: 10.

In a preferred embodiment, the recombinant viral genome comprises the nucleotide sequence SEQ ID NO: 11. Specifically, the 5' AAV ITR comprises nucleotides 1-133, the HCR/hAAT promoter comprises nucleotides 199-1292, the intron comprises nucleotides 1336-1420, the mouse BMP4 cDNA insert comprises nucleotides 1557-2794, the SV40 polyA comprises nucleotides 2820-2986 and the 3' AAV ITR comprises nucleotides 3145-3285 of SEQ ID NO: 11.

In another embodiment, the recombinant viral genome comprises the nucleotide sequence of human BMP4 cDNA or a functionally equivalent variant thereof. Preferably, said nucleotide sequence is SEQ ID NO: 12.

The adeno-associated viral vector according to the first aspect of the invention may be any AAV comprising a recombinant viral genome wherein said recombinant viral genome comprises an expression cassette comprising a transcriptional regulatory region operatively linked to a nucleotide sequence encoding BMP4 or a functionally equivalent variant thereof with the exception that when the expression cassette comprises in the 5' to 3' direction, (i) a chicken β-actin promoter and cytomegalovirus enhancer, (ii) the Kozak sequence GCCACCATGG (SEQ ID NO: 1), (iii) a nucleotide sequence encoding rat BMP4, (iv) a woodchuck hepatitis B virus post-regulatory element (WPRE), and (v) a bovine growth hormone polyadenilation signal, and said expression cassette is flanked by AAV2 ITRs, then the serotype of the adeno-associated viral vector is not AAV2.

Components (i) to (v) have the meaning typically understood by the person skilled in the art.

The chicken β-actin promoter and cytomegalovirus enhancer forms a combination known as CAG regulatory region (Alexopoulou A. et al. BMC Cell Biology 2008; 9(2):1-11).

The term "Kozak sequence", as used herein, refers to the Kozak consensus sequence in the 5' to 3' direction GCCAC-CATGG (SEQ ID NO: 1) that enhances translation efficiency.

The term "woodchuck hepatitis B virus post-regulatory element" or "WPRE", as used herein, refers to a DNA sequence that, when transcribed, creates a tertiary structure capable of enhancing the expression of a gene (Lee Y, et al., Exp. Physiol. 2005; 90(1):33-37 and Donello J, et al., J. Virol. 1998; 72(6):5085-5092).

The term "bovine growth hormone polyadenilation signal", as used herein, refers to a polyadenylation signal known by the person skilled in the art (Goodwin E. C. and Rottman, F. M. 1992. J Biol Chem, 267:16330-16334).

Modified AAV sequences also can be used in the context of the present invention. Such modified sequences e.g. include sequences having at least about 70%, at least about 75%, at least about 80%, at least about 85%, at least about 90%, at least about 95% or more nucleotide and/or amino acid sequence identity (e.g. a sequence having about 75-99% nucleotide or amino acid sequence identity) to an AAV ITR, Rep or VP of any of the 42 serotypes known and that maintain the function of said components. Assays for determining the function of AAV ITR, Rep or VP are known in the art. Said modified sequences can be used in place of wild-type AAV ITR, Rep or VP sequences.

Pharmaceutical Compositions of the Invention

The AAV vector of the invention can be administered to the human or animal body by conventional methods, which require the formulation of said vectors in a pharmaceutical composition. Thus, in a second aspect, the invention relates to a pharmaceutical composition (hereinafter referred to as "pharmaceutical composition of the invention") comprising an AAV vector according to the first aspect of the invention, wherein the adeno-associated viral vector comprises a recombinant viral genome wherein said recombinant viral genome comprises an expression cassette comprising a transcriptional regulatory region operatively linked to a nucleotide sequence encoding BMP4 or a functionally equivalent variant thereof with the proviso that when the expression cassette comprises a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal, and said expression cassette is flanked by AAV2 ITRs, then the serotype of the adeno-associated viral vector is not AAV2.

All the embodiments disclosed in the context of the adeno-associated viral vectors of the invention are also applicable to the pharmaceutical compositions of the invention.

Said pharmaceutical composition may include a therapeutically effective quantity of the AAV vector of the first aspect of the invention and a pharmaceutically acceptable carrier.

The term "therapeutically effective quantity" refers to the quantity of the AAV vector of the invention calculated to produce the desired effect and will generally be determined, among other reasons, by the own features of the viral vector of the invention and the therapeutic effect to be obtained. The quantity of the viral vector of the invention that will be effective in the treatment of a disease can be determined by standard clinical techniques described herein or otherwise known in the art. Furthermore, in vitro tests can also be optionally used to help identify optimum dosage ranges. The precise dose to use in the formulation will depend on the administration route, and the severity of the condition, and it should be decided at the doctor's judgment and depending on each patient's circumstances. The effective doses can be extrapolated from a pair of response curves to doses derived from model in vitro assay systems or in animals. For systemic administration, a therapeutically effective dose can be initially estimated from in vitro assays. Said information can be used to precisely determine useful doses in humans. The initial doses can also be estimated from in vivo data (e.g. animal models) using techniques well known in the state of the art. Someone with normal experience in the state of the art can easily optimize administration to humans based on the data in animals.

The dosage of the formulation can be measured or calculated as viral particles or as genome copies ("GC")/viral genomes ("vg").

Any method known in the art can be used to determine the genome copy (GC) number of the viral compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome.

Also, the viral compositions can be formulated in dosage units to contain an amount of viral vectors that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. Preferably, the dose of virus in the formulation is $1.0 \times 10^9$ GC, $5.0 \times 10^9$ GC, $1.0 \times 10^{10}$ GC, $5.0 \times 10^{10}$ GC, $1.0 \times 10^{11}$ GC, $5.0 \times 10^{11}$ GC, $1.0 \times 10^{12}$ GC, $5.0 \times 10^{12}$ GC, or $1.0 \times 10^{13}$ GC, $5.0 \times 10^{13}$ GC, $1.0 \times 10^{14}$ GC, $5.0 \times 10^{14}$ GC, or $1.0 \times 10^{15}$ GC.

The terms "pharmaceutically acceptable carrier," "pharmaceutically acceptable diluent," "pharmaceutically acceptable excipient", or "pharmaceutically acceptable vehicle", used interchangeably herein, refer to a non-toxic solid, semisolid, or liquid filler, diluent, encapsulating material, or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art (Fauli i Trillo C, "Tratado de Farmacia Galénica". Ed. Luzán 5, S. A., Madrid, ES, 1993; Gennaro A, Ed., "Remington: The Science and Practice of Pharmacy" 20th ed. Lippincott Williams & Wilkins, Philadelphia, Pa., US, 2003).

The pharmaceutical composition can be formulated in accordance with routine procedures as a pharmaceutical composition adapted for intravenous, subcutaneous, or intramuscular administration to human beings.

The AAV vector may be formulated for parenteral administration by injection (e.g. by bolus injection or continuous infusion). Formulations for injection may be presented in unit dosage form (e.g. in ampoules or in multi-dose containers) with an added preservative. The viral compositions may take such forms as suspensions, solutions, or emulsions in oily or aqueous vehicles, and may contain formulatory agents such as suspending, stabilizing, or dispersing agents. Liquid preparations of the AAV formulations may be prepared by conventional means with pharmaceutically acceptable additives such as suspending agents (e.g. sorbitol syrup, cellulose derivatives or hydrogenated edible fats), emulsifying agents (e.g. lecithin or acacia), non-aqueous vehicles (e.g. almond oil, oily esters, ethyl alcohol or fractionated vegetable oils), and preservatives (e.g. methyl or propyl-p-hydroxybenzoates or sorbic acid). The preparations may also contain buffer salts. Alternatively, the compositions may be in powder form for constitution with a suitable vehicle (e.g. sterile pyrogen-free water) before use. When necessary, the composition may also include a local anaesthetic such as lidocaine to relieve pain at the injection site. When the composition is going to be administered by infiltration, it can be dispensed with an infiltration bottle which contains water or saline solution of pharmaceutical quality. When the composition is administered by injection, a water vial can be provided for injection or sterile saline solution, so that the ingredients can be mixed before administration. Preferably, the pharmaceutically acceptable carrier is saline solution and a detergent such as Pluronic®.

Compositions of the invention may be formulated for delivery to animals for veterinary purposes (e.g. livestock (cattle, pigs, others)), and other non-human mammalian subjects, as well as to human subjects. The AAV vector can be formulated with a physiologically acceptable carrier for use in gene transfer and gene therapy applications.

Also encompassed is the use of adjuvants in combination with or in admixture with the AAV vector of the invention. Adjuvants contemplated include, but are not limited to, mineral salt adjuvants or mineral salt gel adjuvants, particulate adjuvants, microparticulate adjuvants, mucosal adjuvants.

Adjuvants can be administered to a subject as a mixture with the AAV vector of the invention, or used in combination said AAV vector.

The pharmaceutical composition of the invention may be administered locally or systemically. In an embodiment, the pharmaceutical composition is administered near the tissue or organ whose cells are to be transduced. In a particular embodiment, the pharmaceutical composition of the invention is administered locally in liver by injection into the liver parenchyma. In another preferred embodiment, the pharmaceutical composition of the invention is administered systemically.

Systemic administration includes a systemic injection of the AAV vectors of the invention, such as intramuscular (im), intravascular (ie), intra-arterial (ia), intravenous (iv), intraperitoneal (ip), or sub-cutaneous injections. Preferably, the systemic administration is via im, ip, is or iv injection. Most preferably, the AAV vectors of the invention are administered via intravenous injection.

In a preferred embodiment the pharmaceutical compositions of the invention are delivered to the liver of the subject. Administration to the liver may be achieved by any method known in the art, including, but not limited to intravenous administration, intraportal administration, intrabiliary administration, intra-arterial administration, and direct injection into the liver parenchyma. In a preferred embodiment, the pharmaceutical composition is administered intravenously.

The pharmaceutical compositions of the invention may be administered in a single dose or, in particular embodiments of the invention, multiple doses (e.g. two, three, four, or more administrations) may be employed to achieve a therapeutic effect. Preferably, the AAV vector comprised in the pharmaceutical composition of the invention are from different serotypes when multiple doses are required to obviate the effects of neutralizing antibodies.

Therapeutic Methods of the Invention

AAV vectors may be utilized for the purpose of transferring DNA into cells in vivo, particularly for facilitating the delivery of BMP4 to a subject in need thereof by administering the AAV vectors of the invention to the patient, thus generating cells capable of expressing BMP4 in vivo. Since BMP4 is a secreted polypeptide, it can be secreted by the cells, allowing the systemic delivery of BMP4.

In a third aspect, the invention relates to an AAV vector according to the first aspect of the invention or a pharmaceutical composition according to the second aspect of the invention for use in medicine.

The authors of the present invention have demonstrated that increased circulating BMP4 produced by the AAV vectors of the invention can improve the metabolic profile in obesity. They have also shown that fat in the liver and associated fibrosis was also reduced in high fat-fed mice indicating that the AAV vectors of the invention may be useful as gene therapy for non-alcoholic fatty liver disease/non-alcoholic steatohepatitis (NAFLD/NASH) and cirrhosis.

Therefore, the AAV vectors of the invention have been proven useful for the gene therapy of metabolic diseases, particularly obesity, insulin resistance, type 2 diabetes, liver cirrhosis and NAFLD/NASH.

In a fourth aspect, the invention relates to an adeno-associated viral vector comprising a recombinant viral genome wherein said recombinant viral genome comprises an expression cassette comprising a transcriptional regulatory region operatively linked to a nucleotide sequence encoding BMP4 or a functionally equivalent variant thereof or a pharmaceutical composition comprising said viral vector for use in the treatment and/or prevention of a disease selected from the group consisting of obesity, insulin resistance, type 2 diabetes, liver cirrhosis and non-alcoholic fatty liver disease (NAFLD)/non-alcoholic steatohepatitis (NASH).

In another aspect, the invention relates to the use of an adeno-associated viral vector comprising a recombinant viral genome wherein said recombinant viral genome comprises an expression cassette comprising a transcriptional regulatory region operatively linked to a nucleotide sequence encoding BMP4 or a functionally equivalent variant thereof or a pharmaceutical composition comprising said viral vector for the manufacture of a medicament for the treatment and/or prevention of a disease selected from the group consisting of obesity, insulin resistance, type 2 diabetes, liver cirrhosis and non-alcoholic fatty liver disease (NAFLD)/non-alcoholic steatohepatitis (NASH).

In another aspect, the invention provides a method for the treatment and/or prevention of a disease selected from the group consisting of obesity, insulin resistance, type 2 diabetes, liver cirrhosis and non-alcoholic fatty liver disease (NAFLD)/non-alcoholic steatohepatitis (NASH) in a subject in need thereof which comprises the administration to said subject of an adeno-associated viral vector comprising a recombinant viral genome wherein said recombinant viral genome comprises an expression cassette comprising a transcriptional regulatory region operatively linked to a nucleotide sequence encoding BMP4 or a functionally equivalent variant thereof or a pharmaceutical composition comprising said viral vector.

The terms "prevent," "preventing," and "prevention", as used herein, refer to inhibiting the inception or decreasing the occurrence of a disease in a subject. Prevention may be complete (e.g. the total absence of pathological cells in a subject) or partial. Prevention also refers to a reduced susceptibility to a clinical condition.

The term "treat" or "treatment", as used herein, refers to the administration of a an AAV vector or a composition of the invention to control the progression of a disease after its clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state, and remission (both partial and total). The control of progression of the disease also involves an extension of survival, compared with the expected survival if treatment is not applied.

The term "subject", as used herein, refers to an individual or animal, such as a human being, a non-human primate (e.g. chimpanzees and other apes and monkey species), a farm animal (e.g. birds, fish, cattle, sheep, pigs, goats, and horses), a domestic mammal (e.g. dogs and cats), or a laboratory animal (e.g. rodents, such as mice, rats and guinea pigs). The term includes a subject of any age or sex. In a preferred embodiment the subject is a mammal, preferably a human being.

The authors of the present invention have demonstrated that the AAV vectors of the invention administered to high fed-fat mice produce a reduction in the body weight gain (Example 1), a reduced adipocyte size (Example 6) and a change in the phenotype of the subcutaneous adipose cells (Example 8) compared to their controls.

Therefore, in an embodiment the disease to be treated and/or prevented is obesity.

The term "obesity", as used in the present invention, relates to the definition of obesity provided by the WHO based on the body mass index (BMI), which consists of the ratio between the weight of a person (in kg) and the square of their height in meters. According to this criteria, a BMI lower than 18.5 $kg/m^2$ is considered as insufficient weight or thinness, a BMI of 18.5-24.9 $kg/m^2$ is considered a normal weight, a BMI of 25.0-29.9 $kg/m^2$ is considered grade 1 of overweight, a BMI of 30.0-39.0 $kg/m^2$ is considered a grade 2 of overweight and a BMI greater than or equal to 40.0 $kg/m^2$ is considered morbid obesity. Alternatively, there are other methods for defining the degree of obesity of a subject, such as the diameter of the waist measured at the midpoint between the lower limit of the ribs and the upper limit of the pelvis (in cm), the thickness of skin folds, and bioimpedance, based on the principle that a lean mass transmits electricity better than a fatty mass.

The authors of the present invention have demonstrated that the AAV vectors of the invention administered to high fed-fat mice produce an improvement in the metabolic profile of said mice compared to their controls, such as being more glucose tolerant and having lower circulating insulin levels (Example 2) or being more insulin sensitivity (Example 3).

Therefore, in another embodiment the disease to be treated and/or prevented is selected from insulin resistance and type 2 diabetes.

The term "insulin resistance", as used herein, refers to a disorder wherein cells do not respond correctly to insulin. As a result, the body produces more insulin in response to high blood glucose levels. Patients with insulin resistance frequently display high glucose levels and high circulating insulin levels. Insulin resistance is frequently linked to obesity, hypertension, and hyperlipidemia. Additionally, insulin resistance frequently appears in patients with type 2 diabetes.

The term "type 2 diabetes", as used herein, refers to a disease characterized by an inappropriate increase in blood glucose levels. The chronic hyperglycemia of diabetes is associated with long-term damage, dysfunction, and failure of different organs leading to a variety of complications such as retinopathy, nephropathy, and peripheral neuropathy. Type 2 diabetes is caused by insulin resistance in peripheral tissues (principally skeletal muscle, adipose tissue, and liver) and inappropriate compensatory insulin secretion response, due to the combination of decreased β-cell mass and function. In addition to increasing glucose concentration, faulty insulin action frequently translates into an increase in cholesterol or triglyceride levels.

The authors of the present invention have demonstrated that the AAV vectors of the invention administered to high fed-fat mice produce a reduction in liver fat and associated fibrosis of said mice compared to their controls (Examples 10 and 11).

Therefore, in another embodiment, the disease to be treated and/or prevented is selected from the group consisting of liver cirrhosis and NAFLD/NASH, preferably is NAFLD/NASH.

The term "liver cirrhosis", as used herein, relates to a condition in which the liver slowly deteriorates and malfunctions because liver tissue is replaced by fibrous scar tissue and regenerative nodules. This results in a partial block in the flow of blood through the liver as well as in an impairment in the liver's ability to control infections, remove bacteria and toxins from the blood, process nutrients, hormones, and drugs, make proteins that regulate blood clotting and produce bile to help absorb fats (including cholesterol) and fat-soluble vitamins.

The term "NAFLD" or "non-alcoholic fatty liver disease", as used herein, relates to a condition occurring when fat is deposited in the liver (steatosis) not due to excessive alcohol use. It is related to insulin resistance and the metabolic syndrome and may respond to treatments originally developed for other insulin-resistant states (e.g. diabetes mellitus type 2) such as weight loss, metformin and thiazolidindiones. NAFLD ranges from simple steatosis to NASH or to cirrhosis.

The term "NASH" or "non-alcoholic steatohepatitis", as used herein, is the most extreme form of NAFLD, and collectively refers to the state where the liver develops a hepatic disorder (e.g. inflammation, fibrosis, cirrhosis, etc.) or the state where the liver may induce such a pathological condition. NAFLD is regarded as a major cause of cirrhosis of the liver of unknown cause.

The AAV vectors of the invention or the compositions of the invention may be administered locally or systemically.

The term "locally administered", as used herein, means that the AAV vectors or compositions of the invention may be administered to the subject at or near a specific site.

The term "systemically administered" and "systemic administration", as used herein, means that the AAV vectors or compositions of the invention may be administered to a subject in a non-localized manner. The systemic administration of the AAV vectors or compositions of the invention may reach several organs or tissues throughout the body of the subject or may reach specific organs or tissues of the subject. For example, the intravenous administration of an AAV vector or a pharmaceutical composition of the invention may result in the transduction of more than one tissue or organ in a subject.

All the embodiments disclosed in the context of the AAV vectors of the invention and the pharmaceutical compositions of the invention are applicable to the therapeutic methods of the invention.

Particularly, in an embodiment, if the expression cassette of the adeno-associated viral vector comprises a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal, and said expression cassette is flanked by AAV2 ITRs, then the serotype of the adeno-associated viral vector is not AAV2. In another embodiment, the serotype of the AAV is selected from the group consisting of AAV2, AAV5, AAV7, AAV8, AAV9, AAV10 and AAVrh10; more preferably is AAV8. In another embodiment, the transcriptional regulatory region of the expression cassette of the AAV vector comprises a promoter; preferably a constitutive promoter; more preferably a liver-specific promoter; even more preferably the liver-specific promoter is selected from the group consisting of albumin promoter, phosphoenol pyruvate carboxykinase (PEPCK) promoter and alpha 1-antitrypsin promoter; the most preferred being human alpha 1-antitrypsin promoter. In another embodiment, the transcriptional regulatory region of the expression cassette of the AAV vector further comprises an enhancer operatively linked to the promoter; preferably a liver-specific enhancer; more preferably a hepatic control region enhancer (HCR). In another embodiment, the expression cassette of the AAV vector further comprises a polyadenylation signal, more preferably SV40polyA. In another embodiment, the adeno-associated virus ITRs are AAV2 ITRs. In another embodiment, the BMP4 is selected from the group consisting of human BMP4 and mouse BMP4. In another embodiment, the nucleotide sequence encoding mouse BMP4 is selected from SEQ ID NO: 6 and SEQ ID NO: 7. In another embodiment the recombinant viral genome of the AAV comprises a nucleotide sequence selected from SEQ ID NO: 10 and SEQ ID NO: 11. In another embodiment the nucleotide sequence encoding human BMP4 is SEQ ID NO: 8. In another embodiment the recombinant viral genome of the AAV comprises the nucleotide sequence SEQ ID NO: 12.

Polynucleotides, Vectors and Plasmids of the Invention

The invention also relates to polynucleotides which are useful for producing the AAV vectors according to the invention. Thus, in a fifth aspect, the invention relates to a polynucleotide ("polynucleotide of the invention") comprising an expression cassette flanked by adeno-associated virus ITRs wherein said expression cassette comprises a transcriptional regulatory region operatively linked to a nucleotide sequence encoding BMP4 or a functionally equivalent variant thereof with the proviso that said expression cassette is not an expression cassette comprising a chicken β-actin promoter and cytomegalovirus enhancer, the Kozak sequence GCCACCATGG (SEQ ID NO: 1), a nucleotide sequence encoding rat BMP4, a woodchuck hepatitis B virus post-regulatory element (WPRE) and a bovine growth hormone polyadenilation signal.

The term "polynucleotide", as used herein, refers to a nucleic acid molecule, either DNA or cDNA, containing deoxyribonucleotides with the capacity to encode a polypeptide. The polynucleotides of the invention can be obtained using molecular biology techniques well known in the art.

All the embodiments and definitions disclosed in the context of the adeno-associated viral vectors of the invention are applicable to the polynucleotides of the invention.

Particularly, in an embodiment the polynucleotide of the invention comprises a transcriptional regulatory region that comprises a promoter; preferably a constitutive promoter; more preferably a liver-specific promoter; more preferably a liver-specific promoter selected from the group consisting of albumin promoter, phosphoenol pyruvate carboxykinase (PEPCK) promoter and alpha 1-antitrypsin promoter; the most preferred being the human alpha 1-antitrypsin promoter. In another embodiment, the transcriptional regulatory region of the polynucleotide of the invention further comprises an enhancer operatively linked to the promoter, preferably a liver-specific enhancer, more preferably a hepatic control region enhancer (HCR). In another embodiment, the expression cassette of the polynucleotide of the invention further comprises a polyadenylation signal, more preferably the SV40polyA. In another embodiment the transcriptional regulatory region of the polynucleotide of the invention is not an adipose tissue-specific transcriptional regulatory region. In another embodiment, the adeno-associated virus ITRs of the polynucleotide of the invention are AAV2 ITRs. In another embodiment the BMP4 encoded by the polynucleotide of the invention is selected from the group consisting of human BMP4 and mouse BMP4. In another embodiment the nucleotide sequence encoding mouse BMP4 is selected from SEQ ID NO: 6 and SEQ ID NO: 7. In another embodiment the polynucleotide comprises a nucleotide sequence selected from SEQ ID NO: 10 and SEQ ID NO: 11. In another embodiment the nucleotide sequence encoding human BMP4 is SEQ ID NO: 8. In another embodiment the polynucleotide comprises the nucleotide sequence SEQ ID NO: 12.

The polynucleotide of the invention could be incorporated into a vector such as, for example, a plasmid.

Thus, in another aspect, the invention relates to a vector or plasmid comprising the polynucleotide of the invention. In a particular embodiment, the polynucleotide of the invention is incorporated into an adeno-associated viral vector or plasmid.

Preferably, all other structural and non-structural coding sequences necessary for the production of adeno-associated virus are not present in the viral vector since they can be provided in trans by another vector, such as a plasmid, or by stably integrating the sequences into a packaging cell line.

The term "vector", as used herein, refers to a construct capable of delivering, and optionally expressing, one or more polynucleotides of interest into a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. There are no limitations regarding the type of vector that can be used. The vector can be a cloning vector, suitable for propagation and for obtaining polynucleotides, gene constructs or expression vectors incorporated to several heterologous organisms. Suitable vectors include prokaryotic expression vectors (e.g. pUC18, pUC19, Bluescript and their derivatives), mp18, mp19, pBR322, pMB9, CoIE1, pCR1, RP4, phages and shuttle vectors (e.g. pSA3 and pAT28), and eukaryotic expression vectors based on viral vectors (e.g. adenoviruses, adeno-associated viruses as well as retroviruses and lentiviruses), as well as non-viral vectors such as pSilencer 4.1-CMV (Ambion®, Life Technologies Corp., Carslbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

Methods for Obtaining AAV of the Invention

The invention also relates to a method for obtaining the AAV vector of the invention. Said AAV vectors can be obtained by introducing the polynucleotides of the invention into cells that express the Rep and Cap proteins constitutively or wherein the Rep and Cap coding sequences are provided in plasmids or vectors.

Thus, in another aspect, the invention relates to a method for obtaining an adeno-associated viral vector comprising the steps of:
(i) providing a cell comprising a polynucleotide of the invention, AAV Cap proteins, AAV Rep proteins and, optionally, viral proteins upon which AAV is dependent for replication, (ii) maintaining the cell under conditions adequate for assembly of the AAV and (iii) purifying the adeno-associated viral vector produced by the cell.

The production of recombinant AAV (rAAV) for vectorizing transgenes have been described previously (Ayuso E, et al., Curr. Gene Ther. 2010, 10:423-436; Okada T, et al., Hum. Gene Ther. 2009, 20:1013-1021; Zhang H, et al., Hum. Gene Ther. 2009, 20:922-929; and Virag T, et al., Hum. Gene Ther. 2009, 20:807-817). These protocols can be used or adapted to generate the AAV of the invention.

Any cell capable of producing adeno-associated viral vectors can be used in the present invention including mammalian and insect cells.

In one embodiment, the producer cell line is transfected transiently with the polynucleotide of the invention (comprising the expression cassette flanked by ITRs) and with construct(s) that encodes Rep and Cap proteins and provides helper functions. In another embodiment, the cell line supplies stably the helper functions and is transfected transiently with the polynucleotide of the invention (comprising the expression cassette flanked by ITRs) and with construct(s) that encodes Rep and Cap proteins. In another embodiment, the cell line supplies stably the Rep and Cap proteins and the helper functions and is transiently transfected with the polynucleotide of the invention. In another embodiment, the cell line supplies stably the Rep and Cap proteins and is transfected transiently with the polynucleotide of the invention and a polynucleotide encoding the helper functions. In yet another embodiment, the cell line supplies stably the polynucleotide of the invention, the Rep and Cap proteins and the helper functions. Methods of making and using these and other AAV production systems have been described in the art.

In another embodiment, the producer cell line is an insect cell line (typically Sf9 cells) that is infected with baculovirus expression vectors that provide Rep and Cap proteins. This system does not require adenovirus helper genes (Ayuso E, et al., Curr. Gene Ther. 2010, 10:423-436).

The polynucleotide of the invention used in this method has been described previously. Any of the embodiments disclosed in the context of the polynucleotides of the invention is applicable in the context of the methods for obtaining AAV of the invention.

In another embodiment, the transgene delivery capacity of AAV can be increased by providing AAV ITRs of two genomes that can anneal to form head to tail concatamers. Generally, upon entry of the AAV into the host cell, the single-stranded DNA containing the transgene is converted by the host cell DNA polymerase complexes into double-stranded DNA, after which the ITRs aid in concatamer formation in the nucleus. As an alternative, the AAV may be engineered to be a self-complementary (sc) AAV, which enables the viral vector to bypass the step of second-strand synthesis upon entry into a target cell, providing an scAAV viral vector with faster and, potentially, higher (e.g. up to 100-fold) transgene expression. For example, the AAV may be engineered to have a genome comprising two connected single-stranded DNAs that encode, respectively, a transgene unit and its complement, which can snap together following delivery into a target cell, yielding a double-stranded DNA encoding the transgene unit of interest. Self-complementary AAV have been described in the art (Carter B, U.S. Pat. No. 6,596,535, Carter B, U.S. Pat. No. 7,125,717, and Takano H, et al., U.S. Pat. No. 7,456,683).

Preferably, all the structural and non-structural coding sequences (Cap proteins and Rep proteins) are not present in the AAV vector since they can be provided in trans by a vector, such as a plasmid.

The term "Cap protein", as used herein, refers to a polypeptide having at least one functional activity of a native AAV Cap protein (e.g. VP1, VP2, VP3). Examples of functional activities of Cap proteins include the ability to induce formation of a capsid, facilitate accumulation of single-stranded DNA, facilitate AAV DNA packaging into capsids (i.e. encapsidation), bind to cellular receptors, and facilitate entry of the virion into host cells. In principle, any Cap protein can be used in the context of the present invention.

Cap proteins have been reported to have effects on host tropism, cell, tissue, or organ specificity, receptor usage, infection efficiency, and immunogenicity of AAV viruses. Accordingly, an AAV Cap for use in an rAAV may be selected taking into consideration, for example, the subject's species (e.g. human or non-human), the subject's immunological state, the subject's suitability for long or short-term treatment, or a particular therapeutic application (e.g. treatment of a particular disease or disorder, or delivery to particular cells, tissues, or organs). In a preferred embodiment, the Cap protein is derived from the AAV of the group consisting of AAV2, AAV5, AAV7, AAV8, AAV9, AAV10 and AAVrh10 serotypes. In a preferred embodiment, the Cap protein is derived from AAV8.

In some embodiments, an AAV Cap for use in the method of the invention can be generated by mutagenesis (i.e. by insertions, deletions, or substitutions) of one of the aforementioned AAV Caps or its encoding nucleic acid. In some embodiments, the AAV Cap is at least 70%, 75%, 80%, 85%, 90%, 95%, 98%, or 99% or more similar to one or more of the aforementioned AAV Caps.

In some embodiments, the AAV Cap is chimeric, comprising domains from two, three, four, or more of the aforementioned AAV Caps. In some embodiments, the AAV Cap is a mosaic of VP1, VP2, and VP3 monomers originating from two or three different AAV or a recombinant AAV. In some embodiments, a rAAV composition comprises more than one of the aforementioned Caps.

In some embodiments, an AAV Cap for use in a rAAV composition is engineered to contain a heterologous sequence or other modification. For example, a peptide or protein sequence that confers selective targeting or immune evasion may be engineered into a Cap protein. Alternatively or in addition, the Cap may be chemically modified so that the surface of the rAAV is polyethylene glycolated (i.e. pegylated), which may facilitate immune evasion. The Cap protein may also be mutagenized (e.g. to remove its natural receptor binding, or to mask an immunogenic epitope).

The term "capsid", as used herein, refers to the structure in which the viral genome is packaged. A capsid consists of several oligomeric structural subunits made of proteins. For instance, AAV have an icosahedral capsid formed by the interaction of three capsid proteins: VP1, VP2 and VP3.

The term "Rep protein", as used herein, refers to a polypeptide having at least one functional activity of a native AAV Rep protein (e.g. Rep 40, 52, 68, 78). A "functional activity" of a Rep protein is any activity associated with the physiological function of the protein, including facilitating replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome. In a particular embodiment, AAV rep genes derive from the serotypes AAV1, AAV2, AAV4, AAV5, AAV6, AAV7, AAV8, AAV9, AAV10 or AAVrh10; more preferably from an AAV serotype selected from the group consisting of AAV2, AAV5, AAV7, AAV8, AAV9, AAV10 and AAVrh10.

In some embodiments, an AAV Rep protein for use in the method of the invention can be generated by mutagenesis (i.e. by insertions, deletions, or substitutions) of one of the aforementioned AAV Reps or its encoding nucleic acid. In some embodiments, the AAV Rep is at least 70%, 75%, 80%, 85%, 90%, 95%, 98%, or 99% or more similar to one or more of the aforementioned AAV Reps.

In a more preferred embodiment, the AAV Rep and Cap proteins derive from an AAV serotype selected from the group consisting of AAV2, AAV5, AAV7, AAV8, AAV9, AAV10 and AAVrh10.

The expression "viral proteins upon which AAV is dependent for replication", as used herein, refers to polypeptides which perform functions upon which AAV is dependent for replication (i.e. "helper functions"). The helper functions include those functions required for AAV replication including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus E1, E2a, VA, and E4 or herpesvirus UL5, ULB, UL52, and UL29, and herpesvirus polymerase. In a preferred embodiment, the proteins upon which AAV is dependent for replication are derived from adenovirus.

In some embodiments, a viral protein upon which AAV is dependent for replication for use in the method of the invention can be generated by mutagenesis (i.e. by insertions, deletions, or substitutions) of one of the aforementioned viral proteins or its encoding nucleic acid. In some embodiments, the viral protein is at least 70%, 75%, 80%, 85%, 90%, 95%, 98%, or 99% or more similar to one or more of the aforementioned viral proteins.

Methods for assaying the functions of Cap proteins, Rep proteins and viral proteins upon which AAV is dependent for replication are well known in the art.

The genes AAV rep, AAV cap and genes providing helper functions can be introduced into the cell by incorporating said genes into a vector such as, for example, a plasmid, and introducing said vector into the cell. The genes can be incorporated into the same plasmid or into different plasmids. In a preferred embodiment, the AAV rep and cap genes are incorporated into one plasmid and the genes providing helper functions are incorporated into another plasmid. Examples of plasmids comprising the AAV rep and cap genes suitable for use with the methods of the invention include the pHLP19 and pRep6cap6 vectors (Colisi P, U.S. Pat. No. 6,001,650 and Russell D, et al., U.S. Pat. No. 6,156,303).

The polynucleotide of the invention and the polynucleotides comprising AAV rep and cap genes or genes providing helper functions can be introduced into the cell by using any suitable method well known in the art. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In a particular embodiment, the transfection is carried out by means of co-precipitation with calcium phosphate. When the cell lacks the expression of any of the AAV rep and cap genes and genes providing adenoviral helper functions, said genes can be introduced into the cell simultaneously with the polynucleotide of the invention. Alternatively, said genes can be introduced in the cell before or after the introduction of the polynucleotide of the invention. In a particular embodiment, the cells are transfected simultaneously with three plasmids:

1) a plasmid comprising the polynucleotide of the invention
2) a plasmid comprising the AAV rep and cap genes
3) a plasmid comprising the genes providing the helper functions Alternatively, the AAV rep and cap genes and genes providing helper functions may be carried by the packaging cell, either episomally and/or integrated into the genome of the packaging cell.

Step (ii) of the method of the invention involves maintaining the cell under conditions adequate for assembly of the AAV.

Methods of culturing packaging cells and exemplary conditions which promote the release of AAV vector particles, such as the producing of a cell lysate, may be carried out as described in examples herein. Producer cells are grown for a suitable period of time in order to promote the assembly of the AAV and the release of viral vectors into the media. Generally, cells may be grown for about 24 hours, about 36 hours, about 48 hours, about 72 hours, about 4 days, about 5 days, about 6 days, about 7 days, about 8 days, about 9 days, up to about 10 days. After about 10 days (or sooner, depending on the culture conditions and the particular producer cell used), the level of production generally decreases significantly. Generally, time of culture is measured from the point of viral production. For example, in the case of AAV, viral production generally begins upon supplying helper virus function in an appropriate producer cell as described herein. Generally, cells are harvested about 48 to about 100, preferably about 48 to about 96, preferably about 72 to about 96, preferably about 68 to about 72 hours after helper virus infection (or after viral production begins).

Step (iii) of the method of the invention involves purifying the adeno-associated viral vector produced by the cell.

The AAV of the invention can be obtained from both: i) the cells transfected with the polynucleotides of the invention and ii) the culture medium of said cells after a period of time post-transfection, preferably 72 hours. Any method for the purification of the AAV from said cells or said culture medium can be used for obtaining the AAV of the invention. In a particular embodiment, the AAV of the invention are purified following an optimized method based on a polyethylene glycol precipitation step and two consecutive cesium chloride (CsCl) gradients. Purified AAV of the invention can be dialyzed against PBS, filtered and stored at −80° C. Titers of viral genomes can be determined by quantitative PCR following the protocol described for the AAV2 reference standard material using linearized plasmid DNA as standard curve (Lock M, et al., Hum. Gene Ther. 2010; 21:1273-1285).

In a preferred embodiment step (iii) is further carried out by a polyethylene glycol precipitation step or a cesium chloride gradient fractionation.

In some embodiments, the methods further comprise purification steps, such as treatment of the cell lysate with benzonase, purification of the cell lysate over a CsCl gradient, or purification of the cell lysate with the use of heparin sulphate chromatography (Halbert C, et al., Methods Mol. Biol. 2004; 246:201-212).

Various naturally occurring and recombinant AAV, their encoding nucleic acids, AAV Cap and Rep proteins and their sequences, as well as methods for isolating or generating, propagating, and purifying such AAV, and in particular, their capsids, suitable for use in producing AAV are known in the art.

The invention is hereby explained by the following examples which are to be construed as merely illustrative and not limitative of the scope of the invention.

EXAMPLES

Material and Methods
Animals

All animal experiments were approved by the Research Animal Ethics Committee at the University of Gothenburg, Sweden, with ethics diary numbers 148-2012 and 60-2014. 3-4 weeks old male C57BL6/N mice were purchased from Taconic, Denmark. Mice were group caged, and kept on a 12h light-dark cycle in a temperature- and humidity controlled room. Diet and drinking water were administered ad libitum, and the mice were fed either a 45% kcal high fat diet or 10% kcal low fat diet. The animals were kept on diets for 16 to 17 weeks before termination.

AAV Production and Purification

The genome of AAV2 was used and the virus was pseudotyped with AAV8.

The AAV plasmids used in this study contain an expression cassette flanked by two ITRs from AAV2. The expression cassette has the following elements in the 5' to 3' direction: the liver-specific enhancer hepatic control region (HCR), the liver-specific promoter human alpha anti-trypsin (hAAT), an intron, the mouse BMP4 cDNA and the SV40 polyadenilation signal. This expression cassette is flanked by the 5' ITR and the 3' ITR from AAV2. This construct was named ITR hAAT mBMP4 ITR (FIG. 1) having sequence SEQ ID NO: 11.

The vectors were constructed according to molecular biology techniques well known in the art.

Briefly, pmBMP4 plasmid (GeneArt), containing mouse BMP4 cDNA was digested with XhoI and MluI obtaining two fragments having 1240 bp and 2360 bp. The 1240 bp insert fragment was cloned into pGG2 hAAT plasmid previously digested with XhoI and MluI. The vector plasmid obtained was named pGG2 hAAT mBMP4.

A non-coding plasmid carrying the same components of the ITR hAAT mBMP4 ITR construct, but without the mouse BMP4 cDNA and having a multicloning site was used to produce null particles as a control.

Infectious AAV vector particles were generated in HEK293 cells cultured in roller bottles, by co-transfecting each roller bottle with 125 µg of the vector plasmid pGG2 hAAT mBMP4 (containing the ITRs and the expression cassette) together with 125 µg of the rep/cap plasmid (expressing capsid proteins of the AAV particle and proteins necessary for virus replication), and 150 µg of the helper plasmid pWEAD expressing adenovirus helper functions by calcium phosphate coprecipitation (rep/cap and pWEAD plasmids were kindly provided by Dr. High, Children's Hospital of Philadelphia, USA). A total of 10 roller bottles were used for each vector preparation. Three days after transfection, cells were harvested and centrifuged at 2500 g for 10 min. Cell pellet and medium were then processed separately. Cell pellet was thoroughly reconstituted in TBS (50 mM TrisHCl, 150 mM NaCl, 2 mM MgCl2, pH 8.0). After 3 freeze/thaw cycles the lysate was centrifuged at 2500 g for 30 min. Supernatant from this centrifugation was added to the medium and vector particles were precipitated by incubation with 8% of PEG 8000 (Sigma) for 15 h and pelleted at 2500 g for 30 min. This pellet, now containing vectors from cells and medium, was thoroughly reconstituted in TBS, treated with benzonase (Merck) for 30 min at 37° C. and centrifuged at 10000 g for 10 min. The supernatant was loaded into 37.5 ml ultra clear tubes (Beckman) containing 1.3-1.5 g/ml CsCl density step gradient, and centrifuged for 17 hours at 28.000 rpm in a SW28 rotor (Beckman). Viral bands were carefully collected using a 10 ml syringe and 18-gauge needle and transferred to a new 12.5 ml ultraclear tube, which was filled up with 1.379 g/ml CsCl solution to generate a continuous gradient. Tubes were centrifuged at 38.000 rpm in SW40Ti rotor (Beckman) for 48 hours. Finally, the band of full particles was collected and dialyzed in PBS using 10 KDa membrane (Slide-A-Lyzer Dialysis Products, Pierce) and filtered with 0.45 µm Millipore filters. This PEG and CsCl-based purification protocol dramatically reduces empty AAV capsids and DNA and protein impurities from the viral stock thus increasing AAV purity, which ultimately results in higher transduction in vivo.

The same protocol was used for generating infectious AAV particles carrying the "null" vector.

AAV Virus Vector Injection

Adeno-associated virus vectors (AAV serotype eight) were used to create an over-expression of the secreted protein Bone Morphogenetic Protein 4 (BMP4) in the liver. At six weeks of age mice received a retro-orbital injection of approx. $5 \times 10^{11}$ virus particles per mouse (dissolved in 200 µl NaCl).The injected vectors were either empty "null" (control group) or carried the BMP4 gene, with expression under control of the human alpha 1-antitrypsin promoter (study group). The mice were briefly anesthetized with isofluorane prior to injection.

Glucose Tolerance Test

At study week 11 mice received an intraperitoneal glucose injection (1 g/kg body weight) after four hours of fasting. Tail blood glucose was measured at baseline and 5, 15, 30, 60, 90 and 120 minutes post-injection. Tail vein serum samples were harvested at baseline and 5, 15, 30 and 60 minutes post-injection.

Insulin Tolerance Test

At study week 12 mice received an intraperitoneal insulin injection (0.8 U/kg body weight) after four hours of fasting. Tail blood glucose was measured at baseline and 15, 30, 60, 90 and 120 minutes after injection. Tail vein serum samples were harvested at baseline and 120 minutes post-injection.

Dual-Energy X-Ray Absorptiometry (DEXA)

A DEXA scan was performed at study week 16, using a PIXlmus Mouse Densitometer (Lunar). Mice were briefly anesthetized with isofluorane prior to scan.

β3 Agonist Treatment

After 11 weeks of high-fat feeding, mice received injections with the β3 agonist CL316,243 (Sigma Aldrich) to mimic sympathetic nervous input. Mice received intraperitoneal injections of 1 mg per kg body weight daily for seven days. CL316,243 was diluted in NaCl, and control animals received injections of only NaCl. For the cohort of mice that underwent β3 agonist treatment, termination was performed directly after the seven days of injections.

Termination

Animals were anesthetized with isofluorane, and the neck was dislocated. Blood was sampled using heart puncture before the heart was separated from the animal. Tissues were weighed, before being snap frozen in liquid nitrogen or put in formalin for fixation. One of the two depots of both the epididymal and subcutaneous fat were kept for subsequent adipocyte isolation.

Adipocyte Isolation and Cell Size Measurement

Subcutaneous and epididymal adipose tissue biopsies were digested with collagenase and cell size measured as described (Rotter V. et al. 2003. J Biol Chem, 278, 45777-45784).

Gene Expression Analysis mRNA was prepared from subcutaneous and epididymal adipose tissue using the RNeasy Lipid Tissue Mini Kit (Qiagen) according to provided protocol. mRNA from gastrocnemius and liver was prepared using RNeasy Fibrous Tissue Mini Kit (Qiagen) according to provided protocol. cDNA was prepared from mRNA using the High-Capacity Reverse Transcription cDNA kit (Applied Biosystems, Life Technologies). Real Time RT-PCR gene expression analysis was performed as previously described using the TaqMan System (Applied Biosystems) (Grunberg J R et al. 2014. J Biol Chem 289, 6899-6907).

Morphology and Immunohistochemistry

Formalin-fixed, paraffin embedded tissues were dehydrated and sectioned (6 μm sections for adipose tissue, 4 μm sections for liver) and underwent haematoxylin-eosin staining for morphology. For immunohistochemical staining of subcutaneous adipose tissue, a primary antibody against UCP1 (1:1000, ab10983 (AbCam)), was used. The ABC system and DAB (both from Vector Laboratories) were used for visualization, and sections were counterstained using haematoxylin.

Serum Insulin

Serum insulin levels were measured using the Ultra Sensitive Mouse Insulin ELISA Kit (Crystal Chem, Inc), according to provided protocol.

Statistics

Statistics were performed using IBM SPSS Statistics version 20, and calculated using Mann-Whitney non-parametric U-test. Significances are indicated in figures or in text, B=$p<0.1$, *=$p<0.05$, =$p<0.01$, *=$p<0.001$.

Results

Figure 2:
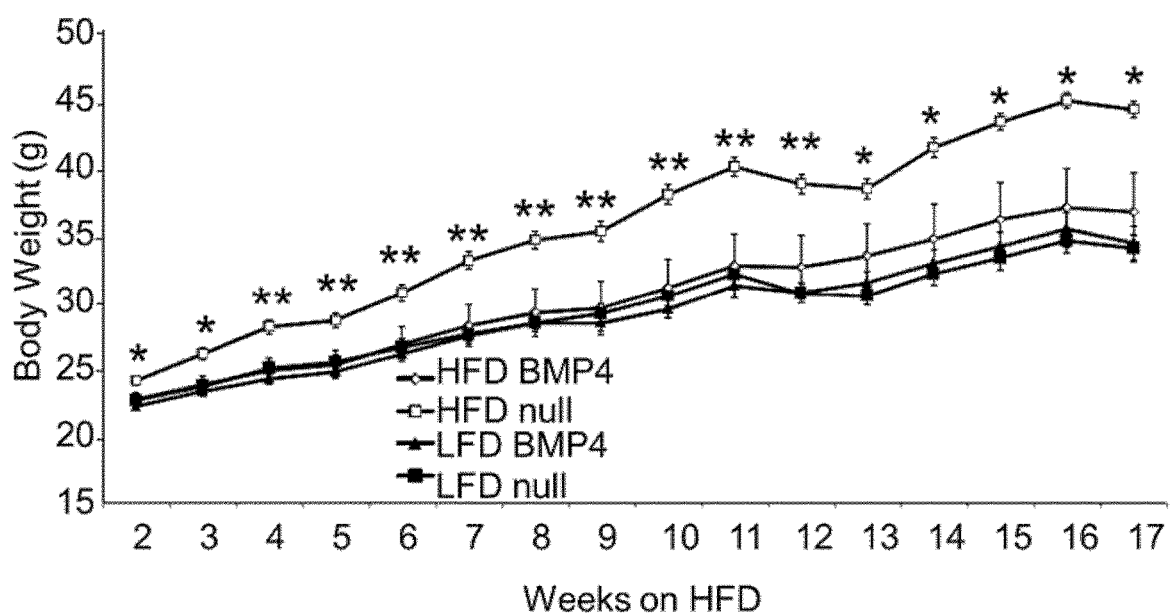
FIG. 2. Body weight. Body weight of mice injected with AAV expressing BMP4 and fed with a high fat diet (HFD BMP4) or with a low fat diet (LFD BMP4) was compared to body weight of mice injected with empty AAV and fed either with a high fat diet (HFD null) or with a low fat diet (LFD null). * $p<0.05$; ** $p<0.01$ FIG. 3. Glucose tolerance test. Glucose and insulin measurements after glucose tolerance test performed in mice injected with AAV. A) Absolute glucose levels. B) Glucose percentage of initial fasting level. C) Circulating insulin levels. n=11-21. IP, intraperitoneal injection. Min., minutes. B $p<0.1$; * $p<0.05$;  $p<0.01$; * $p<0.001$ FIG. 4. Insulin tolerance test. Glucose measurements after insulin tolerance test performed in mice injected with AAV. A) Absolute glucose levels. B) Glucose percentage of initial fasting level. n=11-21. IP, intraperitoneal injection. Min., minutes. B $p<0.1$; * $p<0.05$;  $p<0.01$; * $p<0.001$ FIG. 5. DEXA Body Composition Scan. Lean tissue mass and fat mass of high fat-fed mice injected with AAV expressing BMP4 or with empty AAV. A) Absolute tissue mass. B) Percentage of tissue mass. n=11-21. B.W., body weight. * $p<0.05$; ** $p<0.01$ FIG. 6. Adipose tissue mass. Epididymal (EPI), subcutaneous (SC) and mesenteric (MES) fat depots and also brown adipose tissue mass (BAT) were weighted after termination of high fat-fed mice injected with AAV expressing BMP4 or with empty AAV. n=11-21. * $p<0.05$; ** $p<0.01$ FIG. 7. Adipocyte size. Adipocyte size measured in epididymal (Epi) and subcutaneous (SC) isolated cells from high fat-fed mice injected with AAV expressing BMP4 or with empty AAV. n=11-21. * $p<0.05$; ** $p<0.01$ FIG. 8. Endogenous expression of BMP4. Gene expression of endogenous BMP4 in subcutaneous adipose tissue (SC fat), liver and gastrocnemius skeletal muscle was measured by real time RT-PCR. RQ, relative quantification. n=6-10. B $p<0.1$ FIG. 9. Expression of beige/brown adipose cell markers. Gene expression of beige/brown adipocyte markers were measured in subcutaneous adipose tissue by real time RT-PCR. A) HFD BMP4 compared to HFD null, after 16 weeks on high fat diet. n=9-11. B) HFD BMP4+β3 stimulation compared to HFD BMP4+vehicle saline (veh), after 12 weeks of high fat diet. n=8-10. RQ, relative quantification. B $p<0.1$; * $p<0.05$;  $p<0.01$; * $p<0.001$ FIG. 10. Anti-UCP1 immunohistochemistry on formalin-fixed, paraffin-embedded subcutaneous adipose tissue biopsies. Areas of multilobular, UCP1 positive adipocytes were found in HFD-BMP4 mice (two out of five individuals) (A) as compared to HFD-null mice (B) where these were not found. Furthermore, the adipocyte size was clearly reduced in all HFD-BMP4 mice compared to HFD-null mice. Primary antibody was omitted in negative controls (C). 10× objective used for photo. n=5.

Example 1. HFD-BMP4 Mice Gain Less Weight than HFD-Null Throughout the Study, Despite Similar Food Intake Mice fed with a high fat diet (HFD) or with a low fat diet (LFD) were injected either with AAV expressing BMP4 or with AAV null and were weighted weekly during the whole study. Results showed that the BMP4 high fat-fed mice had a similar food intake as the null high fat-fed mice but they increased less in body weight suggesting increased energy expenditure (FIG. 2). No difference was seen in the chow-fed groups.

Figure 3:
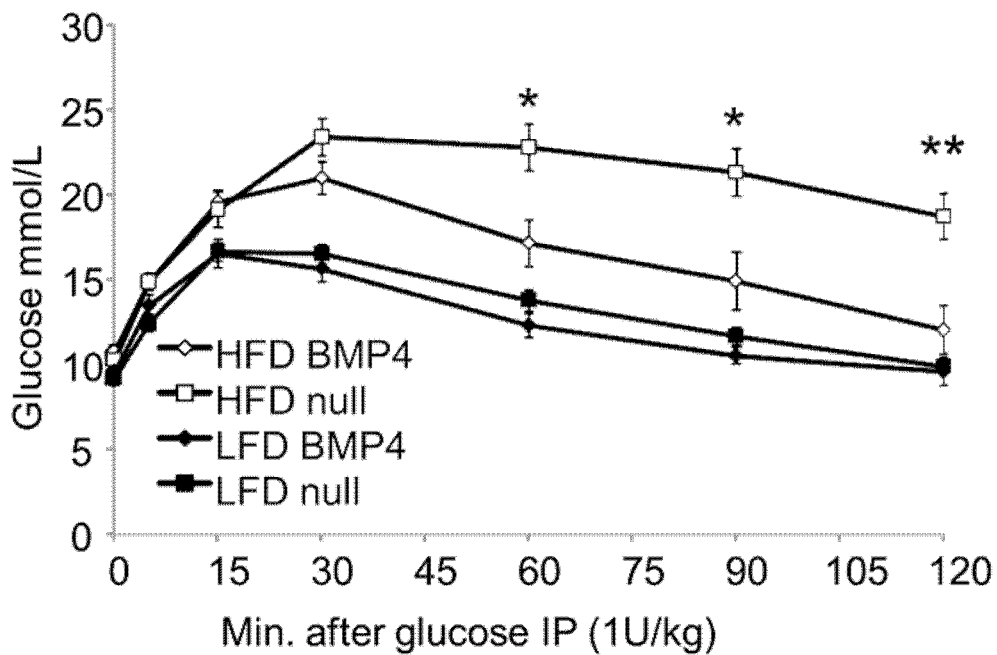
Figure 3:
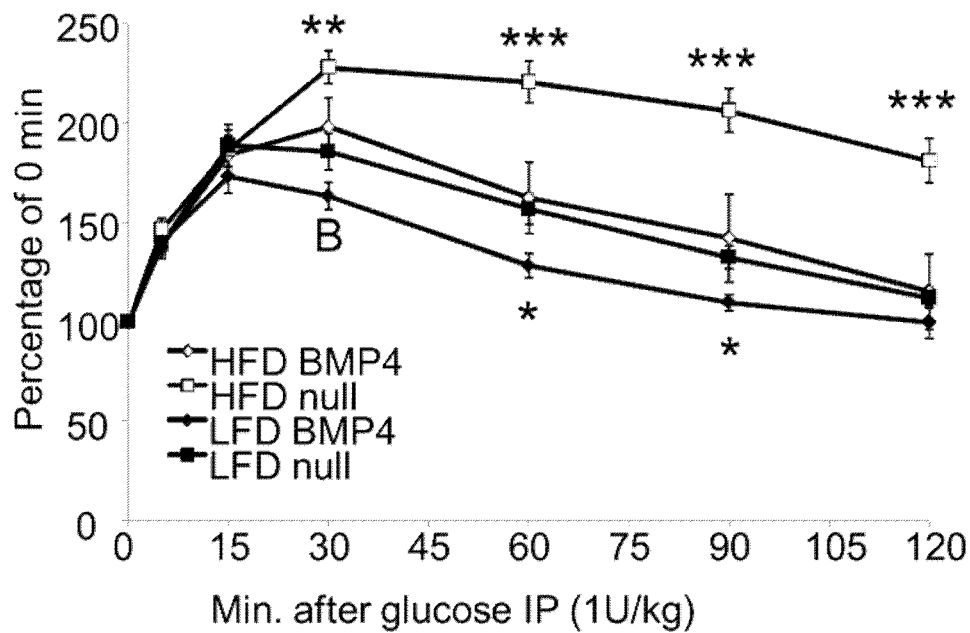
Figure 3:
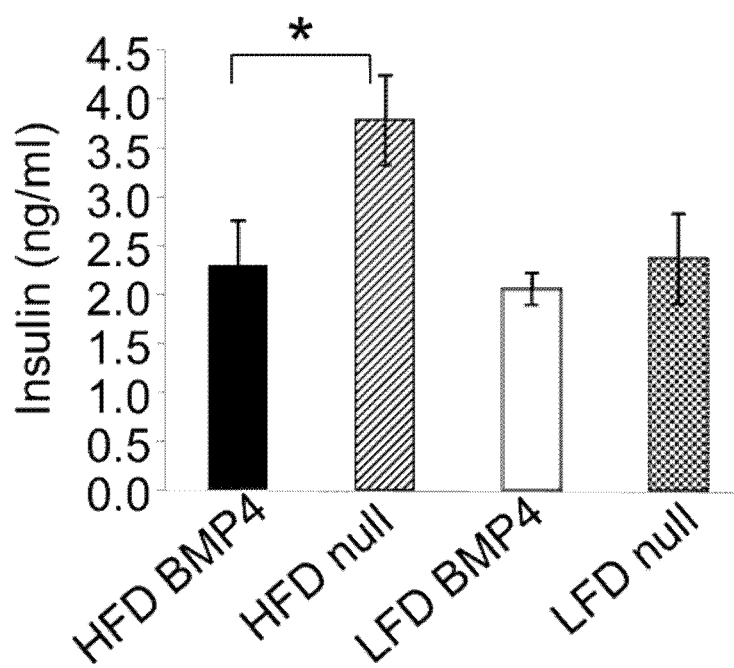

Example 2. HFD-BMP4 Mice are More Glucose Tolerant and have Lower Circulating Insulin Levels than HFD-Null Mice, Comparable to LFD-Fed Mice At study week 11 a glucose tolerance test was performed by intraperitoneal glucose injection in mice after four hours of fasting. Tail blood glucose was measured at baseline and at different times after glucose injection. The BMP4 high fat fed-mice had an improved glucose tolerance compared to the null high fat fed-mice both when expressed as absolute glucose levels (FIG. 3A) or as percentage of initial fasting level (FIG. 3B). In fact, they had a similar glucose tolerance as chow-fed null mice but even in the chow-fed group the BMP4 mice had a better glucose tolerance (FIG. 3B).

Circulating insulin levels were measured 15 minutes post-glucose injection. Consistent with an improved insulin sensitivity, the BMP4 high fat-fed mice had lower insulin levels than null high fat-fed mice (FIG. 3C). HFD BMP4 insulin levels are comparable to those obtained in the chow-fed group.

Figure 4:
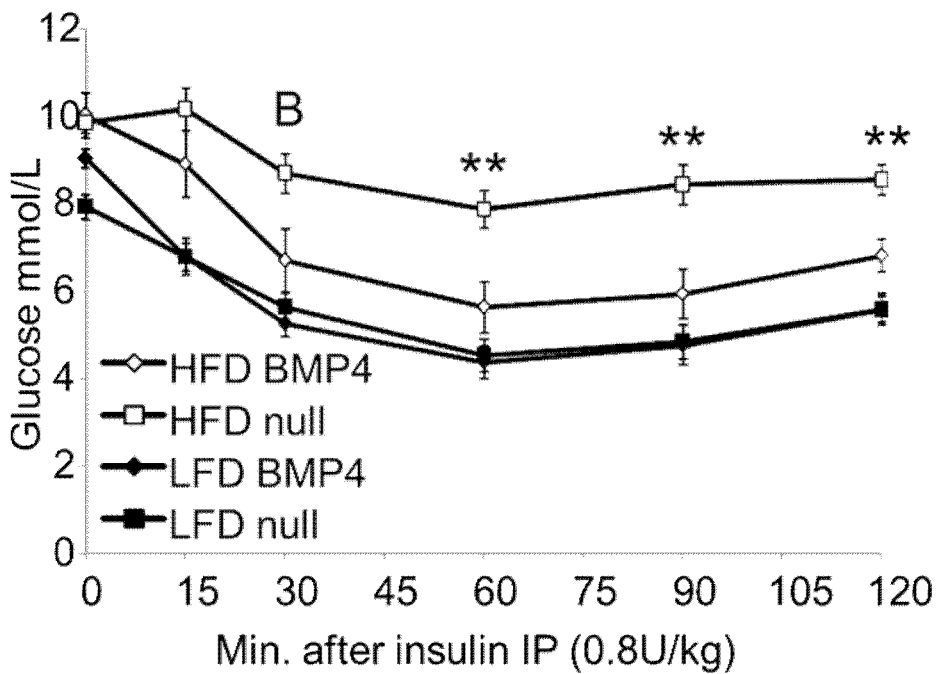
Figure 4:
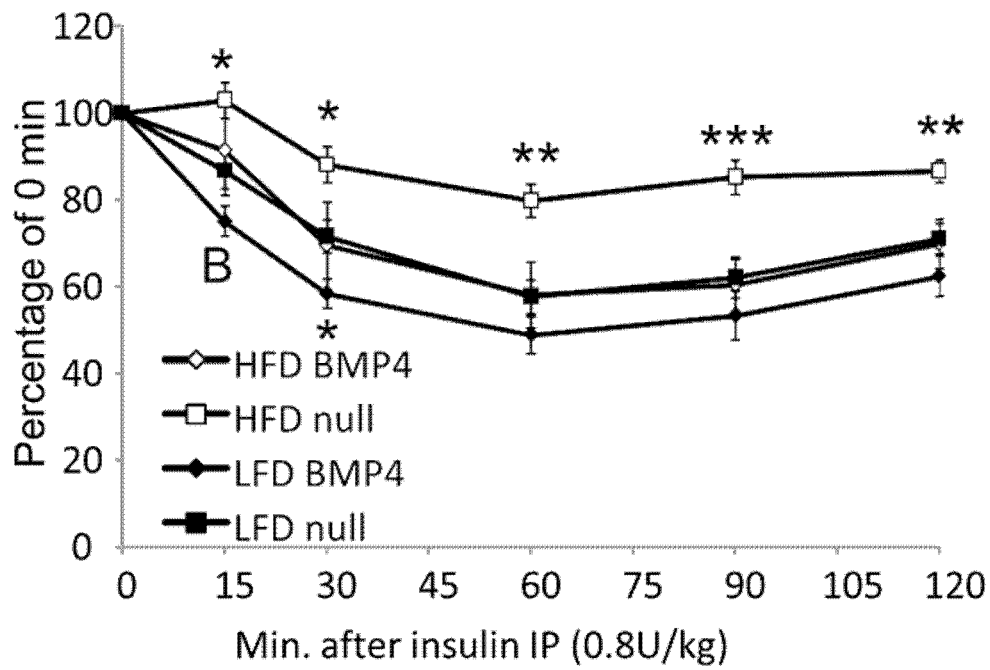

Example 3. HFD-BMP4 Mice are More Insulin Sensitive than HFD-Null Mice, Comparable to LFD-Fed Mice At study week 12 an insulin tolerance test was performed by intraperitoneal insulin injection in mice after four hours of fasting. Tail blood glucose was measured at baseline and at different times after insulin injection. The insulin tolerance tests clearly showed that the BMP4 high fat-fed mice were more insulin sensitive measured as the ability of a given insulin dose to lower the blood glucose levels (FIG. 4A). This was also seen when the insulin effect was related to the fasting glucose levels expressed as percentage of initial glucose level (FIG. 4B). Again, the BMP4 high fat-fed mice behaved similar to the chow-fed and considerably leaner mice.

Figure 5:
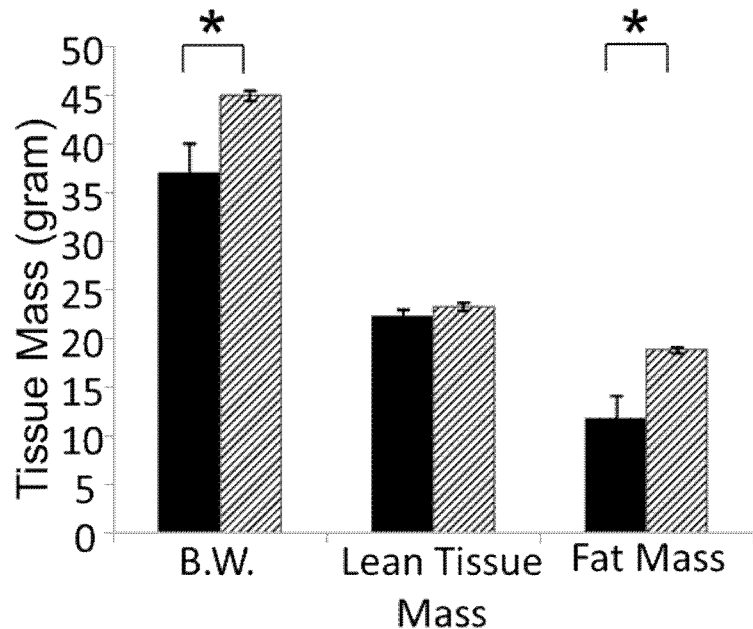
Figure 5:
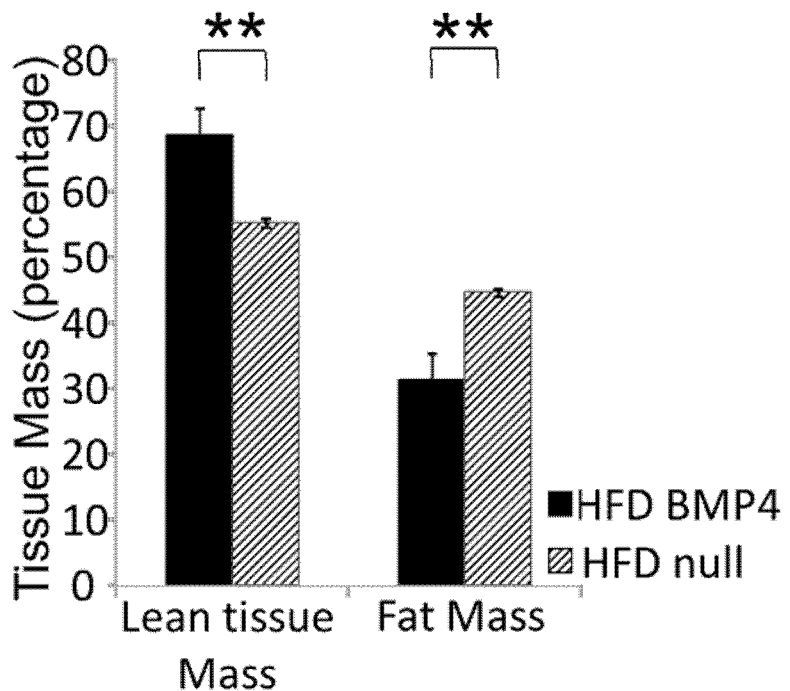

Example 4. HFD-BMP4 Mice have Less Fat Mass and More Lean Tissue Mass than HFD-Null Mice At study week 16 a DEXA Body Composition Scan was performed. DEXA scans identified that the high fat-fed BMP4 mice had a lower body weight and less fat mass but there was no difference in lean body mass (FIG. 5A). When expressed as percentage the high fat-fed BMP4 mice had a significantly greater lean body mass and less fat mass (FIG. 5B).

Example 5. HFD-BMP4 Mice have Reduced Adipose Tissue Mass than HFD-Null Mice

Figure 6:
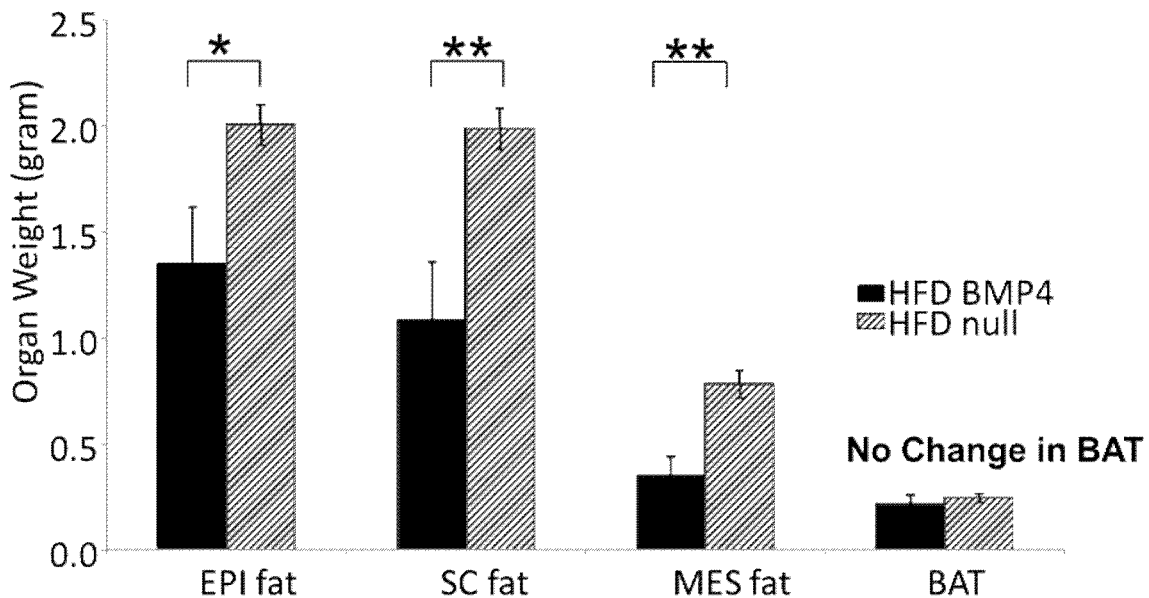

Epididymal, subcutaneous and mesenteric fat depots were weighted upon termination. The reduced body fat in high fat-fed BMP4 mice was reflected in all three measured fat depots. However, and importantly, there was no difference in amount of brown fat mass between the BMP4 and null high fat-fed mice (FIG. 6).

Example 6. HFD-BMP4 Mice have Reduced Adipocyte Size than HFD-Null Mice

Figure 7:
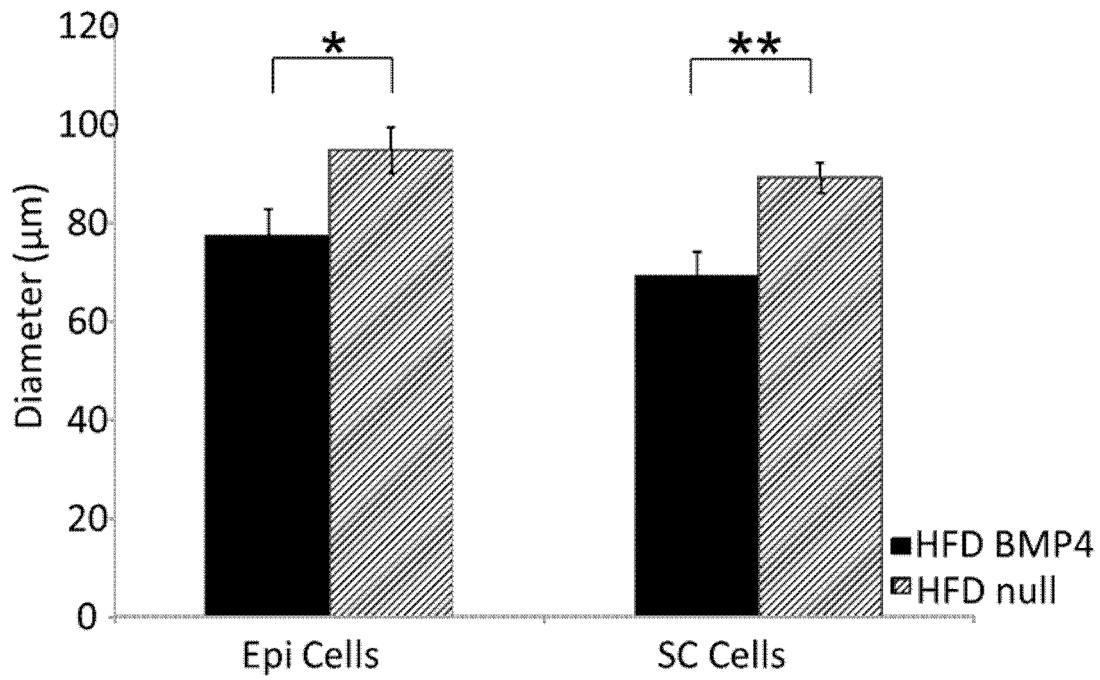

After termination, adipocytes were isolated from subcutaneous and epididymal fat depots and cell diameters were measured. Adipose cell size was also smaller in the fat depots in the BMP4 vs null high fat-fed mice (FIG. 7).

Example 7. Endogenous Expression of BMP4 was Not Affected by Virus Injections

Figure 8:
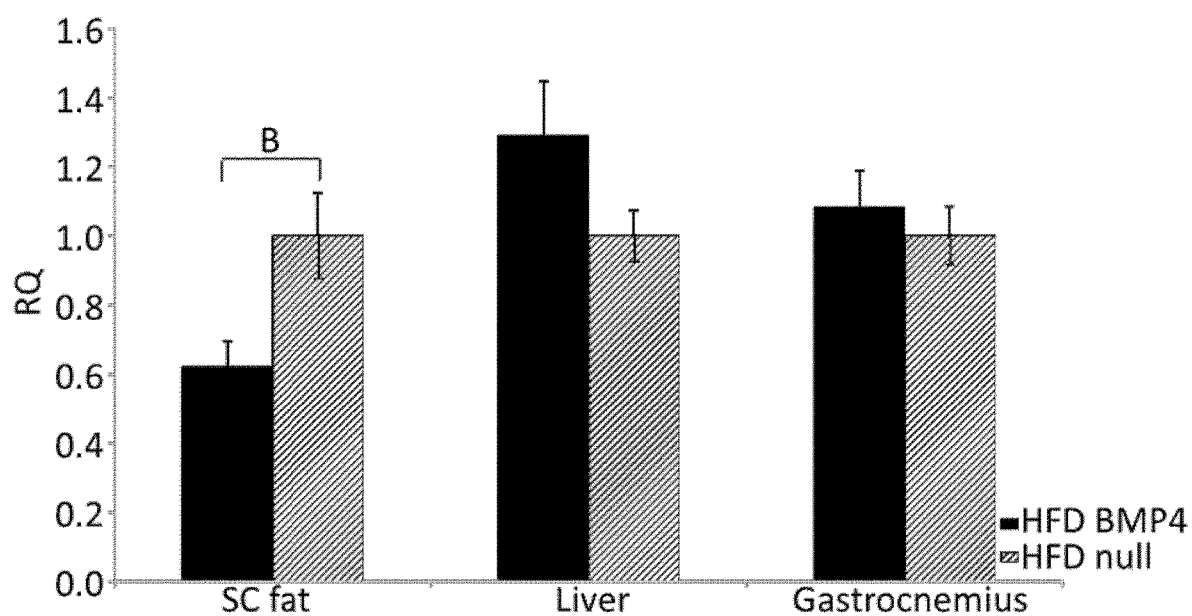

To examine if the increased hepatic BMP4 expression and secretion altered the endogenous cellular BMP4 levels, we analyzed BMP4 mRNA levels in the subcutaneous adipose tissue, liver and gastrocnemius skeletal muscle but no significant differences were seen. A slight and trivial tendency ($p<0.1$) was seen in the subcutaneous fat (FIG. 8).

Example 8. Induction of Beige/Brown Markers in Subcutaneous Adipose Tissue of HFD-BMP4 Mice The authors of the present invention examined mRNA levels of beige/brown adipose cell markers in the white subcutaneous adipose tissue of BMP4 high fat-fed mice to explore the possibility that a changed phenotype towards a more oxidative subcutaneous adipose tissue could account for the lower body weight and the improved insulin sensitivity. A shown in FIG. 6, there was no difference in the brown adipose tissue mass.

Figure 9:
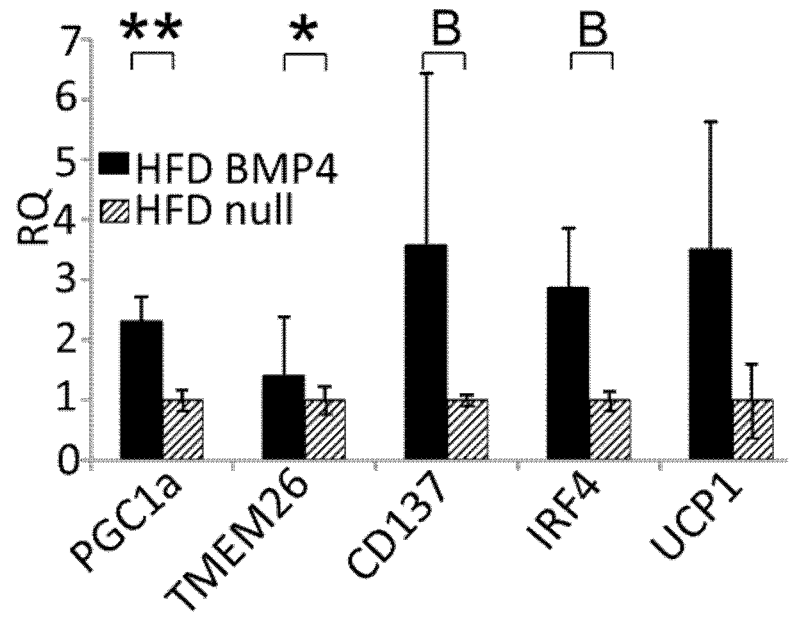
Figure 9:
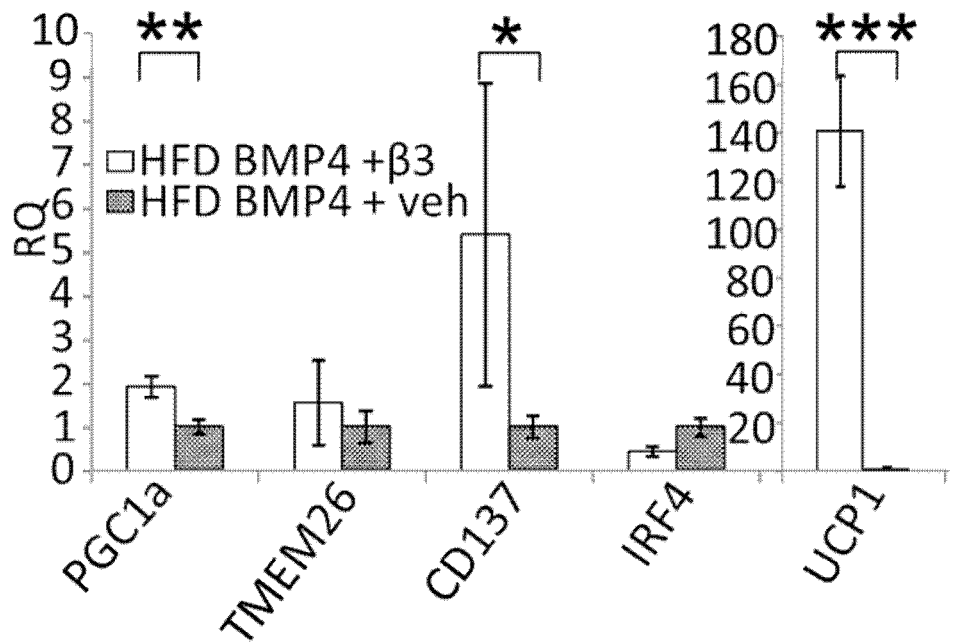

The data shown in FIG. 9A show that the subcutaneous adipose tissue of HFD-BMP4 mice expressed higher levels of the mitochondrial regulator PGC1α as well as the beige markers TMEM26, CD137, IRF4 and the classical brown marker UCP1 as compared to HFD-null mice. To explore the possibility that the subcutaneous adipose tissue could be further activated by cAMP towards a brown oxidative state, HFD-BMP4 mice were injected with a β3-agonist for 7 days and compared to HFD-BMP4 mice injected with saline vehicle. As shown in FIG. 9B there was a dramatic increase in the brown adipose marker UCP1 while the beige markers were less affected in HFD-BMP4 mice injected with the β3-agonist. These data clearly document that the BMP4 high fat-fed mice exhibited an oxidative subcutaneous adipose tissue although still able to accumulate and store fat in the cells.

Figure 10:
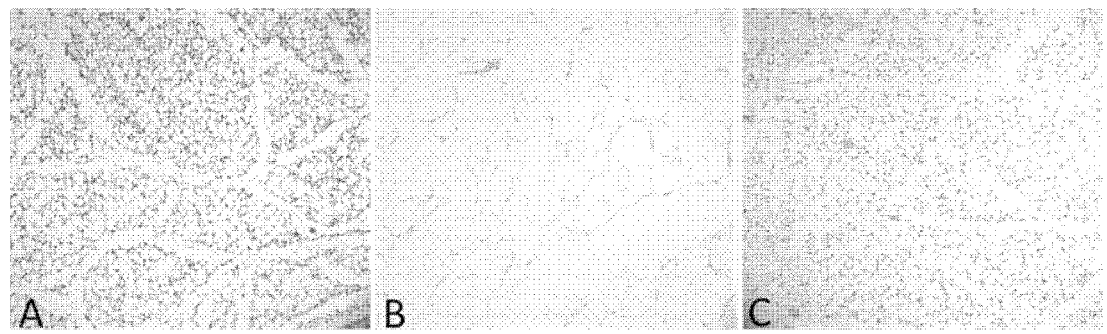

Example 9. Islets of Multilobular, UCP1-Positive Adipocytes Identified in HFD-BMP4 Mice Subcutaneous adipose tissue from HFD-BMP4 and HFD-null mice was stained for immunohistochemistry with a primary antibody against UCP1. UCP1 protein was identified in the subcutaneous adipose tissue in the BMP4 high fat-fed mice even before they were treated with the β3 agonist (FIG. 10A). The adipocyte size was clearly reduced in HFD-BMP4 mice compared to BMP4-null mice.

Example 10. Reduced Fibrosis in Subcutaneous Fat of HFD-BMP4

Figure 11:
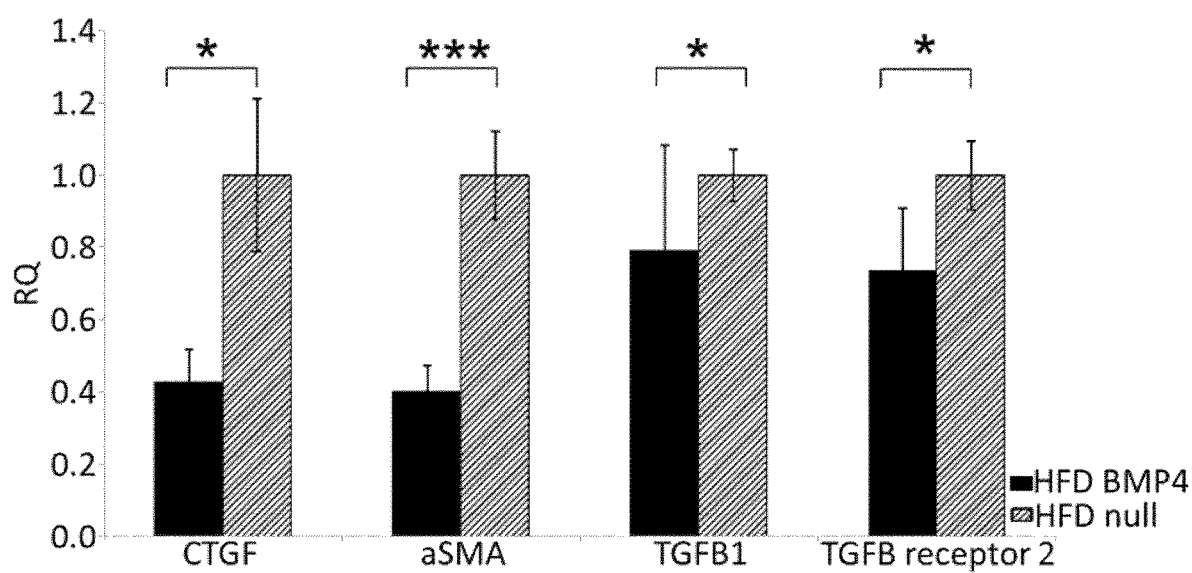
FIG. 11. Expression of markers of fibrosis. Gene expression of markers of fibrosis was measured in subcutaneous adipose tissue of HFD-BMP4 and HFD-null mice by real time RT-PCR. n=9-11. RQ, relative quantification. * $p<0.05$; *** $p<0.001$ FIG. 12. Hematoxylin-eosin morphology staining of formalin-fixed, paraffin-embedded liver from HFD-BMP4 mice (A) and HFD-null mice (B). n=4. 10× objective used for photo.

The inventors examined if the development of fibrosis was different in the mouse models HFD-BMP4 and HFD-null. Fibrosis is a well-known effect of obesity and is considered to negatively influence adipose tissue function. The authors found that mRNA levels of several markers of ongoing fibrosis were reduced in the subcutaneous adipose tissue in BMP4 high fat-fed mice as compared to null high fat-fed mice (FIG. 11). This is consistent with an anti-fibrotic effect of BMP4.

Example 11. Markedly Reduced Liver Fat Accumulation in HFD-BMP4 Mice

Figure 12:
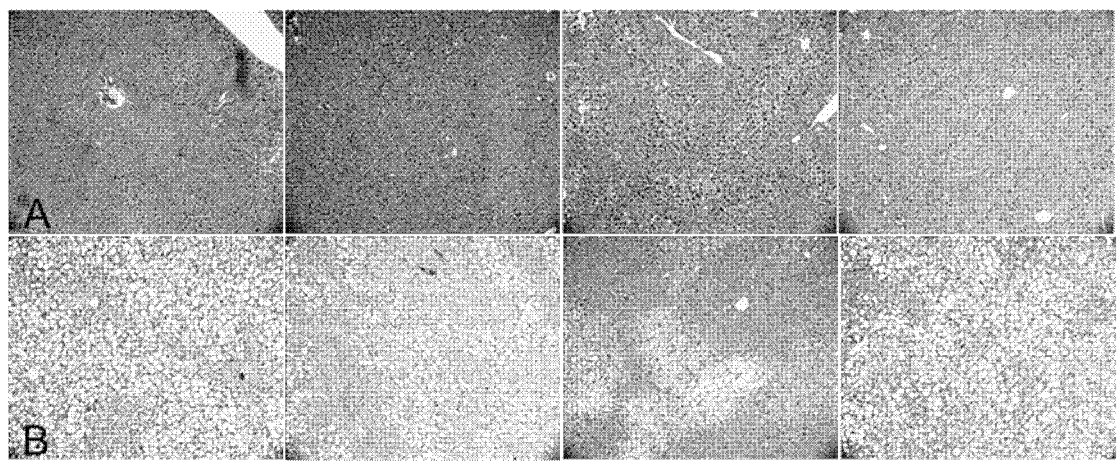

It is well-known that obesity and high-fat feeding leads to increased fat accumulation in the liver and that this induces inflammation and risk for the serious condition of NASH (non-alcoholic steatohepatitis) and liver cirrhosis. Liver biopsies from HFD-BMP4 and HFD-null mice were stained for morphology and it was shown that the null high fat-fed mice accumulated much fat in their liver (FIG. 12B) but the BMP4 high fat-fed mice were dramatically protected from this (FIG. 12A).

Example 12. Improved Oxidative Phenotype in Skeletal Muscle of HFD-BMP4 Mice

Figure 13:
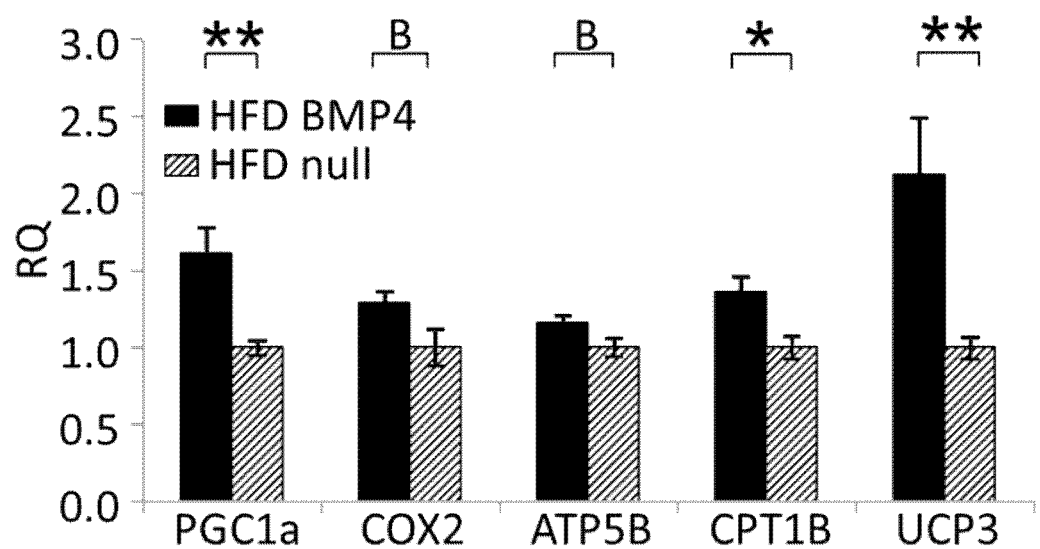
FIG. 13. Expression of oxidative genes. Gene expression of various oxidative genes was measured in skeletal muscle (gastrocnemius) of HFD-BMP4 and HFD-null mice by real time RT-PCR. n=6-7. RQ, relative quantification. B $p<0.1$; * $p<0.05$; ** $p<0.01$

It was also examined if the skeletal muscles were influenced by the increased circulating BMP4. This would be consistent with findings shown in FIG. 5 that HFD-BMP4 mice have more percentage lean body mass. Interestingly, several markers of an oxidative phenotype were found in the BMP4 high fat-fed mice when compared to the null mice (FIG. 13). These results suggest that the muscle have increased numbers of mitochondria.

CONCLUSIONS

The authors have found that increased BMP4 levels secreted by the liver and thereby reaching target tissues through the blood stream induce a positive phenotype in obese mice. The authors have used a gene therapy approach by inducing BMP4 secretion by the liver in fully mature and developed mice and have shown that this produces a markedly beneficial effect and prevents obesity-associated metabolic complications or, in man, the metabolic syndrome. In spite of becoming obese on a high-fat diet the BMP4 mice increased the induction of beige and brown adipose cells in the adipose tissue leading to increased insulin sensitivity and improved glucose tolerance. Data also indicates that inflammation in the adipose tissue is reduced, which is known to enhance insulin sensitivity. Remarkably, the authors have found that fat accumulation in the liver (NAFLD) was markedly less in the BMP4 mice and the fibrosis in the liver was reduced as well (NASH). Most liver lipids were dramatically reduced. The authors have also found that BMP4 is anti-fibrotic.

Therefore, the authors have demonstrated that increasing BMP4 in the bloodstream via the liver by using an AAV vector encoding BMP4 is a potential approach for gene therapy in obesity/insulin resistance/type 2 diabetes and also when this is associated with NAFLD/NASH.

The invention claimed is:

1. A method of treatment and/or prevention of obesity, insulin resistance, type 2 diabetes, liver cirrhosis and/or non-alcoholic fatty liver disease (NAFLD)/non-alcoholic steatohepatitis (NASH) wherein an adeno-associated viral vector is administered, said adeno-associated viral vector comprising a recombinant viral genome wherein said recombinant viral genome comprises an expression cassette flanked by adeno-associated virus ITRs comprising a transcriptional regulatory region operatively linked to a nucleotide sequence encoding BMP4 having a degree of identity of at least 80% to SEQ ID NO 6 or 7 or 8, wherein the transcriptional regulatory region comprises an alpha 1-antitrypsin promoter.

2. A method according to claim 1, wherein the transcriptional regulatory region further comprises a Hepatic Control Region (HCR) enhancer operatively linked to the promoter.

3. A method according to claim 1, wherein the expression cassette further comprises a polyadenylation signal.

4. A method according to claim 1, wherein the adeno-associated virus ITRs are AAV2 ITRs.

5. A method according to claim 1, wherein BMP4 is selected from the group consisting of human BMP4 and mouse BMP4.

6. A method according to claim 1, wherein the recombinant viral genome comprises:
   (a) a nucleotide sequence selected from SEQ ID NO: 10 and SEQ ID NO: 11, or
   (b) the nucleotide sequence SEQ ID NO: 12.

7. A method according to claim 1, wherein the adeno-associated viral vector is comprised in a pharmaceutical composition.

8. A method of treatment and/or prevention of obesity, insulin resistance, type 2 diabetes, liver cirrhosis and/or non-alcoholic fatty liver disease (NAFLD)/non-alcoholic steatohepatitis (NASH) wherein a polynucleotide is administered, said polynucleotide comprising an expression cassette flanked by adeno-associated virus ITRs wherein said expression cassette comprises a transcriptional regulatory region comprising an alpha 1-antitrypsin promoter operatively linked to a nucleotide sequence encoding BMP4 having a degree of identity of at least 80% to SEQ ID NO 6 or 7 or 8.

9. A method according to claim 8, wherein the transcriptional regulatory region further comprises a Hepatic Control Region (HCR) enhancer operatively linked to the promoter.

10. A method according to claim 8 wherein the expression cassette further comprises a polyadenylation signal.

11. A method according to claim 8 wherein the adeno-associated virus ITRs are AAV2 ITRs.

12. A method according to claim 8 wherein BMP4 is selected from the group consisting of human BMP4 and mouse BMP4.

13. A method according to claim 8 wherein the polynucleotide comprises:
   (a) a nucleotide sequence selected from SEQ ID NO: 10 and SEQ ID NO: 11, or
   (b) the nucleotide sequence SEQ ID NO: 12.

14. A method according to claim 8, wherein the polynucleotide is comprised in a vector or plasmid.

* * * * *